US008808272B2

(12) United States Patent
Barry et al.

(10) Patent No.: US 8,808,272 B2
(45) Date of Patent: Aug. 19, 2014

(54) BIOCOMPATIBLE MEDICAL DEVICES

(75) Inventors: James Barry, Marlborough, MA (US); Maria Palasis, Wellesley, MA (US); Louis Ellis, Orono, MN (US); Timothy Mickley, Elk River, MN (US); Brian Berg, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2459 days.

(21) Appl. No.: 11/451,634

(22) Filed: Jun. 12, 2006

(65) Prior Publication Data

US 2007/0197980 A1   Aug. 23, 2007

Related U.S. Application Data

(63) Continuation-in-part of application No. 10/683,577, filed on Oct. 10, 2003, now abandoned, which is a continuation-in-part of application No. 09/429,178, filed on Oct. 28, 1999, now Pat. No. 6,638,259, and a continuation-in-part of application No. 09/503,586, filed on Feb. 14, 2000, now Pat. No. 6,663,606, application No. 11/451,634, which is a continuation-in-part of application No. 10/909,930, filed on Aug. 2, 2004, which is a continuation of application No. 09/845,092, filed on Apr. 27, 2001, now Pat. No. 6,800,073, which is a continuation-in-part of application No. 09/429,178, filed on Oct. 28, 1999, now Pat. No. 6,638,259, and a continuation-in-part of application No. 09/503,586, filed on Feb. 14, 2000, now Pat. No. 6,663,606.

(51) Int. Cl.
  *A61M 25/00* (2006.01)
(52) U.S. Cl.
  USPC ......... 604/523; 604/265; 604/164.01; 604/19

(58) Field of Classification Search
  USPC .................. 604/96.01, 164.01, 523, 19, 265
  See application file for complete search history.

(56) References Cited

U.S. PATENT DOCUMENTS

| 2,814,296 A | 11/1957 | Everett .......................... 604/265 |
| 3,358,684 A | 12/1967 | Marshall ....................... 604/265 |

(Continued)

FOREIGN PATENT DOCUMENTS

| EP | 0 798 398 A2 | 10/1997 | ................ C23C 8/38 |
| EP | 0810003 A3 | 6/1998 | |

(Continued)

OTHER PUBLICATIONS

Deborah J. Marshall et al., "Biocompatibility of Cardiovascular Gene Delivery Catheters with Adenovirus Vectors: An Important Determinant of the Efficiency of Cardiovascular Gene Transfer," *Molecular Therapy*, vol. 1, No. 5, May 2000, pp. 423-429.

(Continued)

*Primary Examiner* — Edelmira Bosques
(74) *Attorney, Agent, or Firm* — Fish & Richardson P.C.

(57) ABSTRACT

A modified medical device for delivery of a pharmaceutically active material is described. The present inventors have found that many conventional medical devices contain a metallic or polymeric component that comes into contact with a pharmaceutically active material during use, and that the contact substantially reduce the pharmaceutical effectiveness of the pharmaceutically active material. The invention described herein concerns various modifications to the metallic or polymeric component that are effective to diminish such a substantial reduction in pharmaceutical effectiveness.

29 Claims, 18 Drawing Sheets

(56) References Cited

U.S. PATENT DOCUMENTS

| | | | | |
|---|---|---|---|---|
| 3,434,869 A | * | 3/1969 | Davidson | 604/266 |
| 3,598,127 A | | 8/1971 | Wepsic | 604/265 |
| 4,589,873 A | | 5/1986 | Schwartz et al. | 604/265 |
| 4,838,877 A | | 6/1989 | Massau | 604/272 |
| 4,999,210 A | | 3/1991 | Solomon et al. | 427/2 |
| 5,098,977 A | | 3/1992 | Frautschi et al. | 527/313 |
| 5,266,359 A | | 11/1993 | Spielvogel | 427/388.4 |
| 5,328,470 A | * | 7/1994 | Nabel et al. | 604/101.03 |
| 5,368,048 A | | 11/1994 | Stoy et al. | 128/772 |
| 5,385,152 A | | 1/1995 | Abele et al. | 128/772 |
| 5,468,562 A | | 11/1995 | Farivar et al. | 428/457 |
| 5,492,763 A | | 2/1996 | Barry et al. | 428/457 |
| 5,538,510 A | * | 7/1996 | Fontirroche et al. | 604/265 |
| 5,584,821 A | | 12/1996 | Hobbs et al. | 604/280 |
| 5,607,401 A | | 3/1997 | Humphrey | 604/239 |
| 5,637,399 A | | 6/1997 | Yoshikawa et al. | 428/369 |
| 5,643,255 A | | 7/1997 | Organ | 606/41 |
| 5,652,225 A | * | 7/1997 | Isner | 514/44 R |
| 5,671,754 A | | 9/1997 | Schmukler et al. | 128/844 |
| 5,713,860 A | * | 2/1998 | Kaplan et al. | 604/103.01 |
| 5,891,507 A | | 4/1999 | Jayaraman | 427/2.25 |
| 5,928,216 A | | 7/1999 | Spencer | 604/523 |
| 5,947,940 A | | 9/1999 | Beisel | 604/282 |
| 5,997,517 A | | 12/1999 | Whitbourne | 604/265 |
| 6,059,738 A | | 5/2000 | Stoltze et al. | 600/585 |
| 6,080,488 A | | 6/2000 | Hostettler et al. | 428/423.3 |
| 6,096,070 A | | 8/2000 | Ragheb et al. | 623/1 |
| 6,103,037 A | | 8/2000 | Wilson | 156/158 |
| 6,120,536 A | | 9/2000 | Ding et al. | 623/1.43 |
| 6,315,792 B1 | | 11/2001 | Armstrong et al. | 623/1.23 |

FOREIGN PATENT DOCUMENTS

| | | | |
|---|---|---|---|
| JP | 08-257140 | 8/1996 | |
| JP | 11009695 | 1/1999 | |
| JP | 2000254235 | 9/2000 | |
| WO | WO 92/05829 | 4/1992 | A61M 29/00 |
| WO | WO 94/16836 | 8/1994 | B08B 3/12 |
| WO | WO 98/40469 | 9/1998 | C12N 5/12 |
| WO | WO 98/53762 | 12/1998 | A61F 2/06 |
| WO | WO 99/22655 | 5/1999 | A61B 17/32 |
| WO | WO 99/62395 | 12/1999 | |
| WO | WO 00/76573 A1 | 12/2000 | A61M 31/00 |

OTHER PUBLICATIONS

Barry, J. "Standard Specification for Chemical Passivation Treatments for Stainless Steel Parts," American Society for Testing and Materials, Designation A 967-96, 1996, pp. 1-6.

Raininko et al., "Clot Formation in Angiographic Catheters—an in vitro Comparative Study," Acta Radiologica 34 (1993) 78-82.

Maalej et al., "The Potent Platelet Inhibitory Effects of S-Nitrosated Albumin Coating of Artificial Surfaces," Journal of Biomedical Materials Research 21 (1987) 613-627.

Engbers et al., An in vitro Study of the Adhesion of Blood Platelets onto Vascular Catheters. Part I. Journal of the American College of Cardiology 33 (1999) 1408-1414.

* cited by examiner

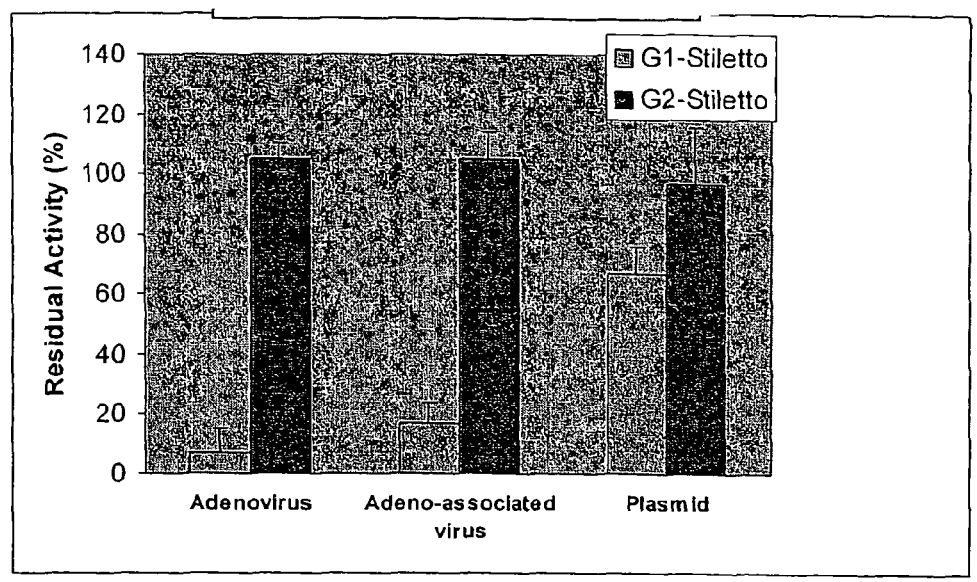
Fig. 14a. Vector Effects
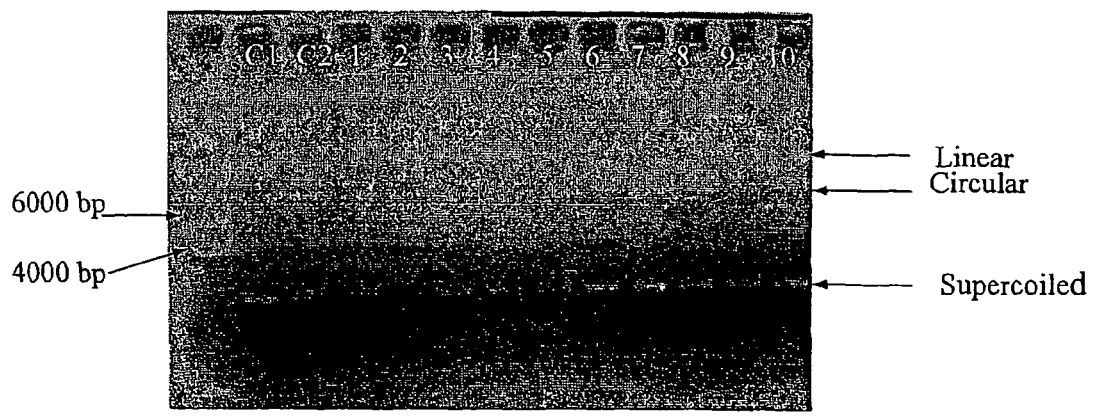
Fig. 14b. Assessment of plasmid DNA structural integrity

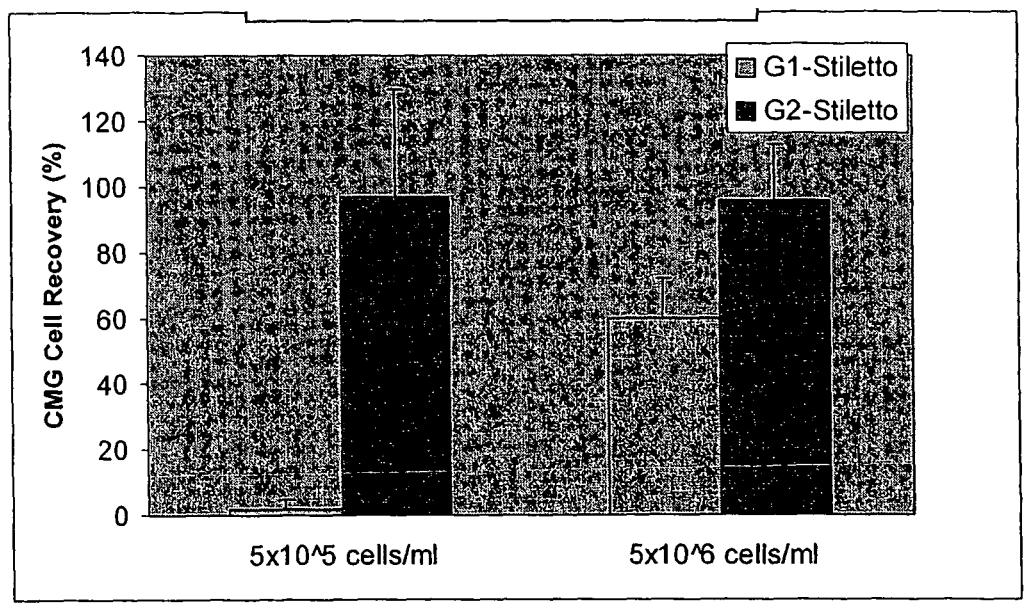

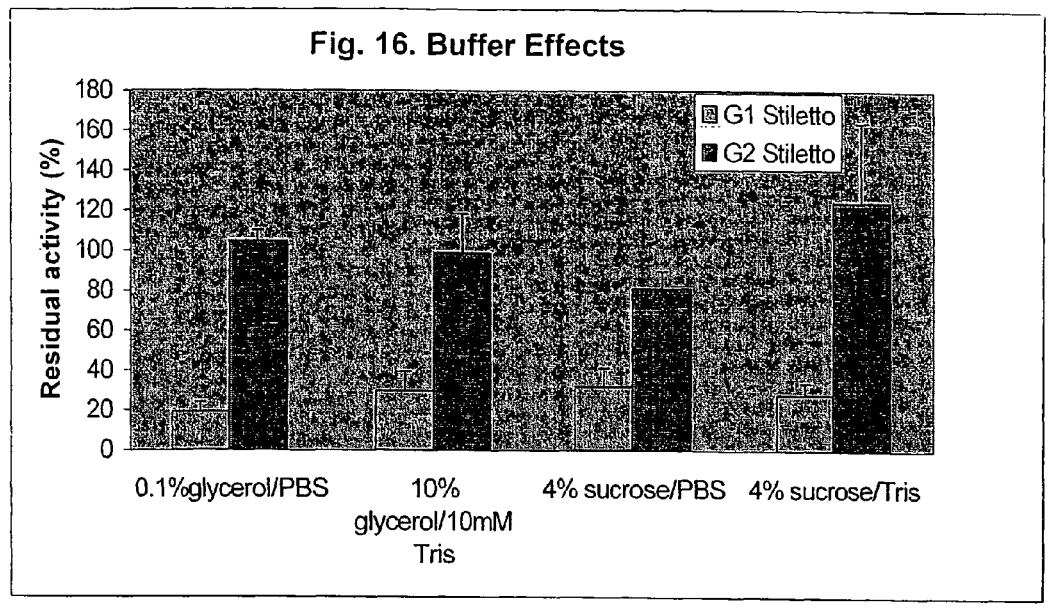
Fig. 16. Buffer Effects
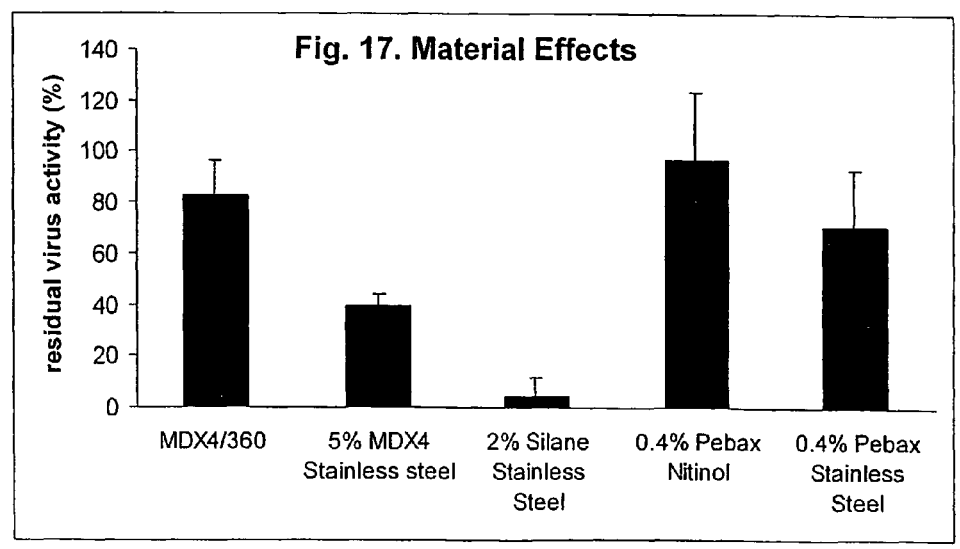
Fig. 17. Material Effects

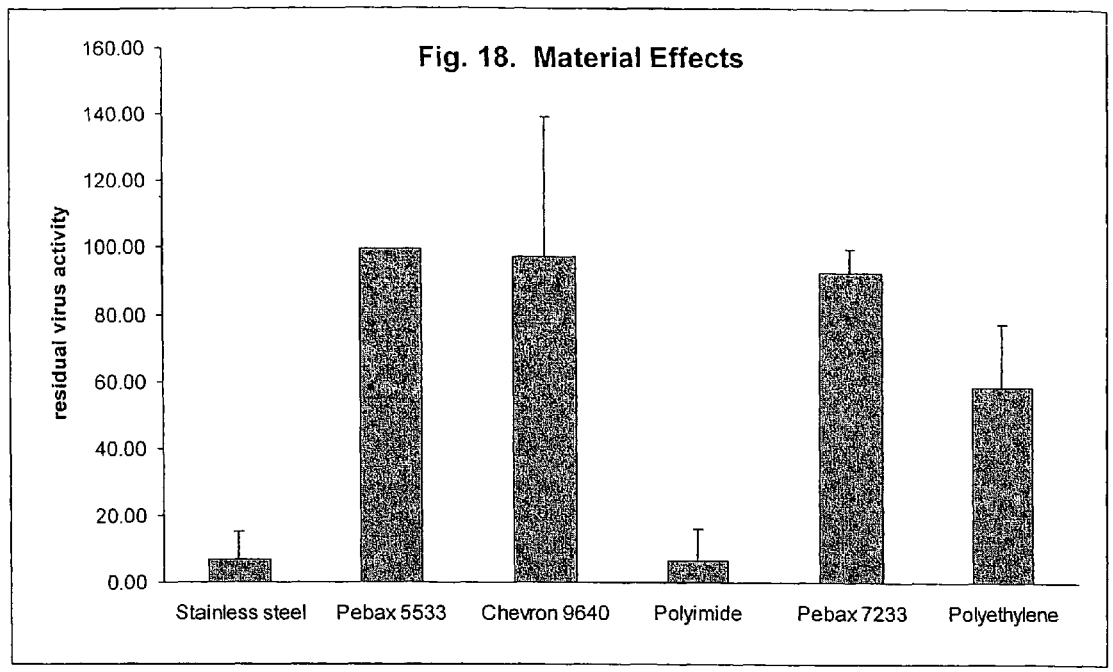
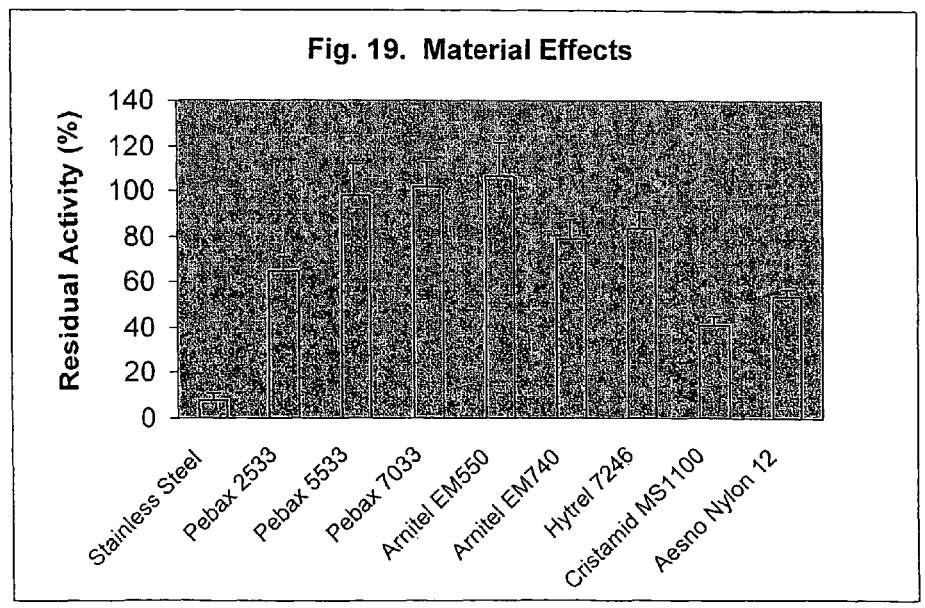

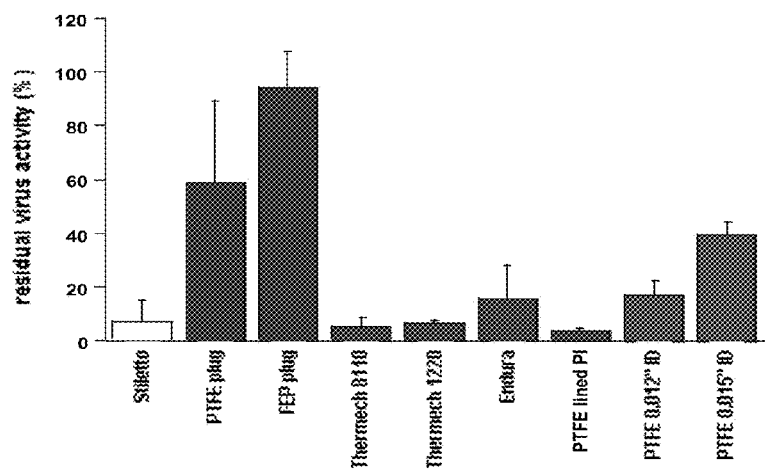
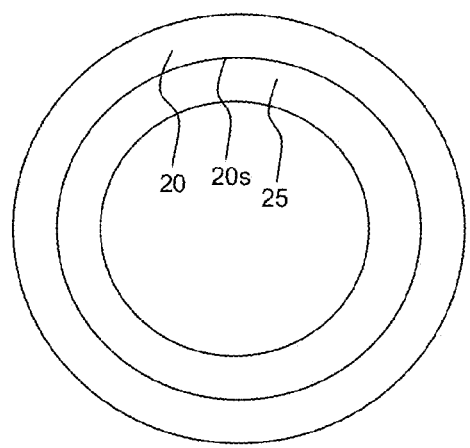

BIOCOMPATIBLE MEDICAL DEVICES

STATEMENT OF RELATED APPLICATIONS

This is a continuation-in-part of U.S. Ser. No. 10/683,577 filed Oct. 10, 2003 now abandoned and entitled "Biocompatible Medical Devices", which is a continuation-in-part of U.S. Ser. No. 09/429,178 filed Oct. 28, 1999, now U.S. Pat. No. 6,638,259, and a continuation-in-part of U.S. Ser. No. 09/503,586 filed Feb. 14, 2000, now U.S. Pat. No. 6,663,606.

This is also a continuation-in-part of U.S. Ser. No. 10/909,930 filed Aug. 2, 2004 and entitled "Biocompatible Pharmaceutical Articles," which is a continuation of U.S. patent application No. 09/845,092, filed Apr. 27, 2001, now U.S. Pat. No. 6,800,073, which is a continuation-in-part of U.S. Ser. No. 09/429,178 filed Oct. 28, 1999, now U.S. Pat. No. 6,638,259 and a continuation-in-part of U.S. Ser. No. 09/503,586 filed Feb. 14, 2000, now U.S. Pat. No. 6,663,606.

Each of the above-referenced applications is incorporated by reference herein in its entirety.

FIELD OF THE INVENTION

The present application relates to medical devices for delivery of pharmaceutically active materials. More specifically, the present invention relates to methods and compositions effective to prevent reduction in the activity of pharmaceutically active materials arising from contact with metallic or polymeric components of medical devices.

BACKGROUND OF THE INVENTION

Medical devices having metallic and polymeric components are used extensively in the medical field. In many cases the medical device is used for delivery of a pharmaceutically active material, and the pharmaceutically active material comes into contact with the metallic or polymeric component during the course of delivery of the pharmaceutically active material.

For example, metallic lumens are frequently used to carry pharmaceutically active materials to various bodily tissues. As another example, metallic stents having a drug delivery polymer coating thereon are used for delivery of pharmaceutically active materials. In both examples, the pharmaceutically active material contacts the metallic component. Metallic components such as stainless steel and nickel-titanium superelastic alloys (e.g., nitinol), cobalt based alloys and super-alloys are commonly used for this purpose as they are formable, have desirable mechanical properties and are commonly believed to be substantially inert.

Moreover, polymeric materials such as polycarbonate, polyimide, acrylonitrile/butadiene/styrene resins (ABS), poly ether ether ketone (PEEK), epoxy and nylon also commonly contact pharmaceutically active materials in connection with their use as catheters, stents, manifolds, stop-cocks, needle materials, and so forth.

The present inventors, however, have found that such materials are relatively incompatible with certain pharmaceutically active materials. As a result, there is at present a need in the art to overcome this incompatibility.

BRIEF DESCRIPTION OF THE FIGURES

FIG. 14a presents activity for various gene vectors after incubation in both an unlined needle injection catheter and an injection catheter lined with polyether block amide.

FIG. 14b presents a structural assessment of plasmid DNA following incubation in both an unlined needle injection catheter and an injection catheter lined with polyether block amide.

FIG. 15 presents the number of viable cells recovered (normalized to a control) obtained after incubation in both an unlined needle injection catheter and an injection catheter that is lined with polyether block amide. Two cell concentrations ($5 \times 10^5$ cells/ml and $5 \times 10^6$ cells/ml) are presented.

FIG. 16 presents virus titer as a percentage of viral stock titer (linear scale) for four adenoviral solutions with differing buffer systems, after incubation in an unlined needle injection catheter and an injection catheter lined with polyether block amide.

FIG. 17 presents virus titer as a percentage of viral stock titer (linear scale) for adenoviral solution after incubation in various lumens.

FIG. 18 presents virus titer as a percentage of viral stock titer (linear scale) for adenoviral solution after incubation in catheters fabricated with various extruded shaft materials.

FIG. 19 presents virus titer as a percentage of viral stock titer (linear scale) for adenoviral solution after incubation in contact with various extruded shaft materials.

FIG. 20 presents virus titer as a percentage of viral stock titer (linear scale) for adenoviral solution after being incubated with various fluorocarbon materials, either as plugs, coatings or liners.

FIG. 21 is a schematic illustration of a polymeric material with a polymeric lumen and an associated layer of polymeric material.

SUMMARY OF THE INVENTION

Figure 1:
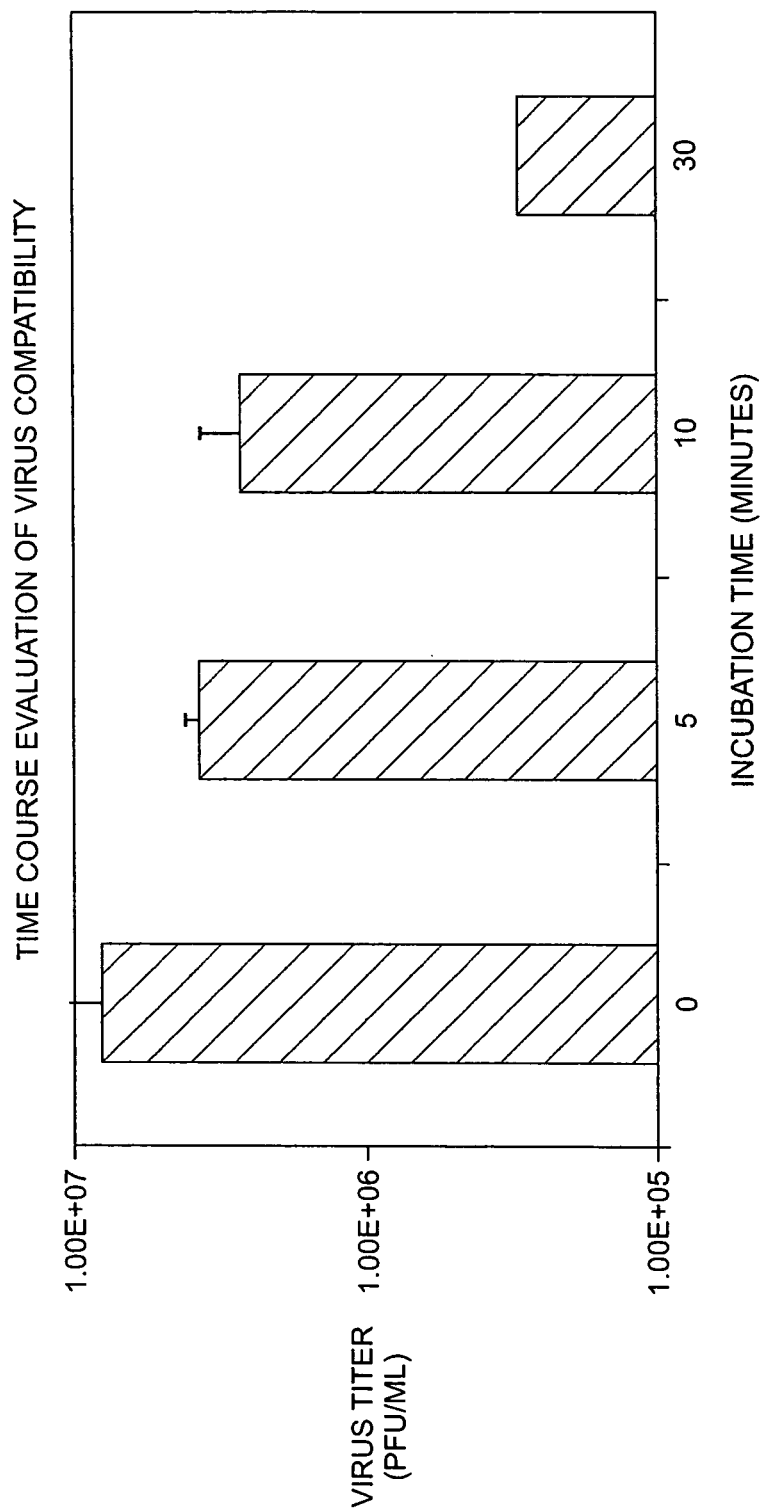
FIG. 1 presents absolute virus titer (log scale) as a function of time for an untreated injection catheter.

According to an embodiment of the invention, a method and modified medical device for delivery of a pharmaceutically active material are provided. The medical device comprises a conventional medical device having a metallic or polymeric component that comes into contact with a pharmaceutically active material, such as a viral vector, during use, such contact acting to substantially reduce the pharmaceutical effectiveness of the pharmaceutically active material. The conventional medical device is thus said to be "incompatible" with the pharmaceutically active material. The incompatible metallic or polymeric component is modified to prevent this substantial reduction in pharmaceutical effectiveness in accordance with the invention.

Numerous devices benefit from the present invention, including medical devices comprising a metallic lumen, such as hypodermic needles and intravascular catheters having an injection lumen, and medical devices that do not have a lumen, such as metallic stents coated with polymer for delivery of the pharmaceutically active material. Examples of metallic components resulting in a substantial reduction in pharmaceutical effectiveness include stainless steel and nitinol. Examples of incompatible polymeric components include polycarbonate, polyimide, acrylonitrile/butadiene/styrene resins (ABS), poly ether ether ketone (PEEK), epoxy and nylon.

Pharmaceutically active materials appropriate for the practice of the present invention are those that benefit from the present invention and include materials comprising polynucleotides, in conjunction with viral or non-viral vectors, proteins, cells, small and large molecule drugs, and so forth.

According to one aspect of the invention, the incompatible polymeric or metallic component is modified by providing it with a surface treatment. Appropriate surface treatments include chemical passivation treatments, such as acid treatment (e.g., treatment with citric acid, nitric acid, etc.) and treatment with steam. Other appropriate surface treatments include treatment with a pharmaceutically acceptable protein, such as albumin, or treatment with a layer of more compatible polymeric material, such as polyethylene (high or low density), polypropylene, polytetrafluoroethylene (PTFE), poly(tetrafluoroethylene-co-hexafluoropropene) (FEP), modified ethylene-tetrafluoroethylene copolymer (ETFE), polyvinylidene fluoride (PVDF), polyethylene terephthalate polyester (PET-P) and so forth. In some embodiments, the polymer is provided as a preformed composition, in other embodiments, the polymer is applied in an uncured form, such as a liquid form, and cured. Still other appropriate surface treatments include treatment with a layer of inorganic material, such as carbon, for example, by means of chemical vapor deposition. Yet other surface treatments involve providing the incompatible metallic or polymeric component with a layer of a more inert metallic material, such as titanium or platinum.

In other embodiments, the incompatible metallic or polymeric component is replaced, for example, with a more compatible metallic or polymeric component, such as gold, titanium and platinum, or with a more compatible polymeric component, such as polyethylene (low or high density), polypropylene, polyethylene terephthalate polyester (PET-P), polyfluorocarbons (e.g., polytetrafluoroethylene (PTFE), modified ethylene-tetrafluoroethylene copolymer (ETFE), poly(tetrafluoroethylene-co-hexafluoropropene) (FEP), polyvinylidene fluoride (PVDF), and so forth), or with an inorganic material such as glass.

One advantage of the present invention is that incompatibility problems that are presently experienced when components of medical devices, including accessories, come into contact with pharmaceutically active materials are minimized.

Another advantage is that the pharmaceutical effectiveness of pharmaceutically active materials that come into contact with device components is not substantially decreased.

Still other embodiments and advantages will become readily apparent to those skilled in the art upon review of the Detailed Description, Examples and Claims set forth below.

DETAILED DESCRIPTION

At present, many medical devices are known in which pharmaceutically active materials pass through metallic or polymeric lumens or otherwise come into contact with metal or plastic prior to delivery to tissue. However, as seen from the examples below, the present inventors have found that where pharmaceutically active materials, specifically viral particles, contact certain metallic or polymeric substrates, including adhesives, pharmaceutical effectiveness is substantially reduced relative to the same materials, which have not come into contact with such substrates. Specifically, the present inventors have found that where pharmaceutically active materials such as viral particles contact metallic materials, such as stainless steel and/or nickel-titanium superalloys such as nitinol, or polymeric materials such as PEEK, polyimide, epoxy, nylon, ABS and/or polycarbonate, viral transfection is substantially reduced, apparently due to inactivation of the virus. This is surprising, since it is normally assumed that such materials are relatively inert and hence unlikely to interact with a pharmaceutically active material.

By "substantially reduced" or "substantial reduction" is meant that pharmaceutical effectiveness is reduced, for example, by at least 5%, more commonly 10%, 20%, 30%, 40%, 50% or more. By "pharmaceutical effectiveness" or "pharmaceutical efficacy" is meant any desired pharmaceutical pharmacological result. For example, a virus having a 10% reduction in pharmaceutical effectiveness is able to infect 10% less cells than it otherwise would. As another example, the pharmaceutical effectiveness of a protein can be measured by its activity through an ELISA assay.

Polymeric or metallic components resulting in such a substantial reduction are referred to herein as "incompatible metallic or polymeric components". Conversely, components that diminish such a reduction in pharmaceutical effectiveness are referred to herein as "more compatible" components.

The present invention overcomes the above and other difficulties by providing medical devices for delivery of pharmaceutically active materials in which the incompatible metallic and/or polymeric components of such devices (including adhesives) that come into contact with the pharmaceutically active materials are modified or replaced with a more compatible component. The devices of the present invention thus do not result in a substantial reduction in pharmaceutical effectiveness.

Conventional (i.e., known) medical devices benefiting from the present invention are numerous and include, for example, catheters, conventional needle syringes, hypodermic needles, biopsy needles and devices, tissue ablation devices, needle injection catheters (for endocardial, epicardial, and pericardial agent administration), filters, grafts, metallic and polymeric stents including those having a polymer coated thereon for delivery of pharmaceutically active materials, aneurysm filling coils, transmyocardial revascularization devices, percutaneous myocardial revascularization devices, soft tissue clips, sutures, blood clot filters, implants or spikes (polymeric or metallic), microspheres or nanoparticles, and so forth. Specific examples of devices for drug delivery to the heart include, for example, those found in the following patents and patent applications: U.S. Pat. No. 5,450,846, U.S. Pat. No. 5,840,059, U.S. Pat. No. 5,878,751, U.S. Pat. No. 5,551,427, U.S. Pat. No. 5,931,834, U.S. Pat. No. 5,925,012, U.S. Pat. No. 5,925,033, U.S. Pat. No. 5,538,504, WO 99/39624, WO 99/44656, WO 99/21510, WO 99/29251, EP A 99-06 0895752, and EP A 99-01 0888750, each of which is incorporated herein by reference. Components of medical devices benefiting from the present invention are numerous and include, for example, adhesives, coatings, balloons, membranes, manifolds, hubs, fittings, etc. Accessory components used in conjunction with medical devices also benefiting from the present invention and include stopcocks, valves, tubing kits, manifolds, wires, syringes, etc.

The medical devices contemplated for use in connection with the present invention can be used for systemic treatment or to treat any mammalian tissue or organ. Non-limiting examples include tumors; organs including but not limited to the heart, lung, brain, liver, kidney, bladder, urethra and ureters, eye, intestines, stomach, pancreas, ovary, prostate; skeletal muscle; smooth muscle; breast, cartilage and bone. The terms "pharmaceutically active materials", "therapeutic agents" and "drugs" are used interchangeably herein and include pharmaceutically active compounds, polynucleotides with and without carrier vectors such as lipids, compacting agents (such as histones), viruses, virus-like particles (i.e., synthetic particles made to act like viruses), polymers, cells, proteins, enzymes, small and large molecule drugs, and the like, with or without targeting sequences. An injection administered in accordance with the present invention includes the pharmaceutically active material and solutions thereof. Pharmaceutically active materials useful in accordance with the present invention may be used singly or in combination.

A "polynucleotide" is a nucleic acid molecule polymer, such as DNA, RNA and their analogs, having as few as 3 nucleotides, and can include both double- and single-stranded sequences. A "protein" is a polymer of as few as two (dimer) amino acid residues.

Preferably, the pharmaceutically active material is a polynucleotide, more preferably in conjunction with virus or virus-like particles. Specific examples of viruses include adenovirus, paroviruses such as adeno-associated virus, lentivirus, retrovirus, alpha-virus, papilloma virus, murine leukemia virus, Semliki Forest virus, etc.

Specific examples of pharmaceutically active materials used in conjunction with the present invention include, for example, pharmaceutically active compounds, cells, proteins, oligonucleotides, ribozymes, antisense oligonucleotides, DNA compacting agents, gene/vector systems (i.e., any vehicle that allows for the uptake and expression of nucleic acids), polynucleotides (including, for example, recombinant nucleic acids; naked DNA, cDNA, or RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposome and cationic polymers that are selected from a number of types depending on the desired application. Cells can be of human origin (autologous or allogeneic) or from an animal source (xenogeneic), genetically engineered if desired to deliver proteins of interest at the transplant site. The delivery media can be formulated as needed to maintain cell function and viability.

Several therapeutic categories and exemplary pharmaceutically active materials follow. Examples include anti-inflammatory agents such as dexamethasone, prednisolone, corticosterone, budesonide, estrogen, sulfasalazine, mesalamine, and analogues thereof; antineoplastic/antiproliferative/antimiotic agents such as paclitaxel, 5-fluorouracil, cisplatin, vinblastine, vincristine, rapamycin, epothilones, endostatin, angiostatin, thymidine kinase inhibitors, and analogues thereof; anesthetic agents such as lidocaine, bupivacaine, ropivacaine, and analogues thereof; anti-coagulants; integrins, chemokines, cytokines and growth factors.

According to one embodiment of the invention, an incompatible metallic or polymeric component of a medical device (including adhesives) is modified by providing it with a surface treatment. All methods of the present invention, including surface treatments, are carried out to prevent a substantial reduction in pharmaceutical efficacy of the pharmaceutically active material.

One form of surface treatment in accordance with the present invention is a chemical passivation treatment. Preferred chemical passivation treatments include those that provide a robust oxide barrier, such as acid treatment with or without treatment with steam at high temperature. Preferred acids for this purpose include citric acid, nitric acid, and chromic acid. According one preferred embodiment, an incompatible metallic component is treated with acid, immediately followed by treatment with steam at high temperature (e.g., by autoclaving). Information concerning chemical passivation of stainless steel can be found, for example, in ASTM Designation: A 967-96 entitled "Standard Specification for Chemical Passivation Treatments for Stainless Steel Parts," the entire disclosure of which is hereby incorporated by reference. Procedures are set forth therein for nitric acid treatment, citric acid treatment, as well as other treatments, including electrochemical treatments.

Other forms of surface treatment include treating the incompatible metallic or polymeric component with solutions containing lipids and liposomes; emulsifying agents and detergents such as glycerin, sodium lauryl sulfate, sodium oleate; proteins, such as, for example, albumin, particularly human serum albumin (HSA) and bovine serum albumin (BSA); other natural polymers such as hyaluronic acid, laminin, fibronectin, fibrin, and collagen, as well as glucans and glycosaminoglycans, such as dextrans, dextran sulfate and heparin; synthetic polymers such as polyethylene glycol, polyethylene oxide, polyvinyl pyrrolidone, SP1017 (Supratek Pharma), polyethylenimine, protamine sulfate, polyamidoamine dendrimers, amphiphilic peptides, RGD-oligolysine peptides, and fluorocarbons such as polytetrafluoroethylene; contrast agents such as iohexol, blood or serum, and so forth. Treatment may be carried out by contacting the agents mentioned above with the incompatible metallic or polymeric component before that component is brought into contact with the therapeutic agent. Treatment may also be carried out by formulating the agents mentioned above directly into the solution or suspension containing the therapeutic agent. For instance, human serum albumin may be formulated into a viral suspension such as adenovirus in order to exert a protective or stabilizing effect. Additionally, the surface treatment may concurrently involve a cleaning process and/or sterilization process to remove surface contaminants or impurities.

Still other forms of surface treatment involve formation of an inorganic layer, for example, amorphous carbon, other diamond-like coatings, or silicone carbide. A preferred method of forming such inorganic layers is chemical vapor deposition (CVD) or physical vapor deposition (PVD). The inorganic layer may also be glass. Surface modifications such as sintering are also possible.

In the case of certain polymeric and other materials of suitable mechanical character, the surface treatment may simply involve the application of a layer of preformed material. As an example, in the case of an incompatible metallic or polymeric lumen, the metallic or polymeric surface can be treated by simply inserting a preformed tube, for example, of a more compatible material into the incompatible metallic or polymeric lumen. For example, with reference to FIG. 21, the a surface 20s of a lumen formed a polymeric material 20 may be provided with a layer of polymeric material 25, which can be, for instance, in the form of a preformed polymeric tube.

Moreover, polymers and other materials can be formed on the metallic or polymeric substrate by any suitable means, such as dipping, spraying, vapor deposition, plasma polymerization and so forth. In many embodiments, a liquid layer is solidified. For example, in the case of polymers, the incompatible metallic or polymeric surface can be treated by forming a polymer layer on the metallic or polymeric component from a liquid layer. Exemplary embodiments for the formation of polymer layers from a liquid layer include (a) formation of a solvent dispersion of a polymer of interest, then coating a surface of the metallic component with the dispersion, followed by removal of solvent, and (b) first coating a surface of the metallic component with a curable polymer resin and subsequently curing the resin, for example, with ultraviolet or infrared radiation.

Hence, polymers appropriate for the practice of the invention include preformed and unformed polymers or hydrogels. Polymers may be crosslinked or uncrosslinked, natural or synthetic, biostable, biodegradable, or dissolvable. These materials may be selected from numerous polymers known in the art. Exemplary polymers are selected from polycarboxylic acids, cellulosic polymers including cellulose acetate and cellulose nitrate, gelatin, polyvinylpyrrolidone, cross-linked polyvinylpyrrolidone, polyanhydrides including maleic anhydride polymers, polyvinyl alcohols, copolymers of vinyl monomers such as EVA (ethylene-vinyl acetate copolymer), polyvinyl ethers, polyvinyl aromatics, polyethylene oxides, glycosaminoglycans, polysaccharides, polyesters including polyethylene terephthalate, polyacrylamides, polyethers, polyether sulfone, polyalkylenes including polypropylene, polyethylene (low and high density) and high molecular weight polyethylene, ethylene vinyl acetate polymers, halogenated polyalkylenes including polytetrafluoroethylene (PTFE), poly(tetrafluoroethylene-co-hexafluoropropene) (FEP), modified ethylene-tetrafluoroethylene copolymer (ETFE), polyvinylidene fluoride (PVDF), and so forth, polyurethanes, polyorthoesters, proteins, polypeptides, silicones, styrene-butadiene polymers, polylactic acid, polyglycolic acid, polycaprolactone, polyhydroxybuterate valerate and blends and copolymers thereof as well as other biodegradable, bioabsorbable and biostable polymers and copolymers. Thermoplastic elastomers such as polyether block amides and styrene-butadiene-styrene are also contemplated. Coatings from polymer dispersions such as polyurethane dispersions (BAYHYDROL, etc.) and acrylic latex dispersions are also within the scope of the present invention. The polymer may be a protein polymer, fibrin, collagen, derivatives of these polysaccharides, an extra cellular matrix component, hyaluronic acid, or another biologic agent or a suitable mixture of any of these, for example. In one embodiment, the polymer is polyacrylic acid, available as HYDROPLUS (Boston Scientific Corporation, Natick Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another embodiment, the polymer is a copolymer of polylactic acid and polycaprolactone.

Preferred polymers include polyethylene (low or high density), polyethylene terephthalate polyester (PET-P), ethylene vinyl acetate polymers, polysulfone, high viscosity acetal homopolymer (such as DELRIN 100), polypropylene, silicone polymers, polyurethanes, styrene-butadiene polymers, polymers such as Poly Penco Ultem 1000 and Hydex 301 Isoplast, fluorinated polyalkenes such as polytetrafluoroethylene (PTFE), poly(tetrafluoroethylene-co-hexafluoropropene) (FEP), modified ethylene-tetrafluoroethylene copolymer (ETFE), polyvinylidene fluoride (PVDF), ethylene chlorotrifluoroethylene copolymer (ECTFE) (such as HALAR 500 HF), and so forth. More preferred polymers include polypropylene, polyethylene (low or high density), PET-P, and fluorinated polymers such as PTFE, ETFE, FEP, and PVDF.

In general, favorable interactions (e.g., ionic, van der Waals, hydrophobic, etc.) between the material and therapeutic agent should be reduced such as to avoid adsorption of the therapeutic agent onto the surface or inactivation or denaturation by the surface.

In other embodiments, the incompatible metallic or polymeric component is replaced with a more compatible component. Exemplary embodiments include replacement of the incompatible metallic or polymeric component with a polymeric component such as those previously discussed. As above, the polymer should be more compatible with the pharmaceutically active material and, of course, the subject into which the pharmaceutically active material is to be introduced. Moreover, the polymer should meet any structural requirements. Numerous methods are available to provide structural integrity or flexibility.

For example, in the event that the medical device comprises a needle (or cannula) for delivery of the pharmaceutically active material, a polymeric needle can be fashioned from several of the materials listed above, notably, PTFE, PET-P, polyphenylene sulfide (PPS), and polysulfone (PS), which have excellent rigidity and the ability to be sharpened into a needle. Additional materials are disclosed in U.S. Pat. No. 4,838,877, including, polyetherimides, polymethylpentenes, polyesters, acrylates, polyaramides, modified phenylene oxides, and polysulfones. Alternatively, where enhanced strength and/or rigidity are desired, the polymeric material can be reinforced, for example, by fibers. For example, U.S. Pat. No. 5,637,399 discloses a synthetic resin needle of reinforced with combustible fibers whose longitudinal directions are arrayed straight or curvilinearly along the axial length of the needle. Numerous resins are listed, from which one or ordinary skill in that art can select and test for compatibility, for example, using the procedures set forth in the Examples. Metal or ceramic reinforcements may be included in addition to combustible fibers.

In still other embodiments, an incompatible metallic or polymeric component is replaced or coated with a more compatible metal. For example, stainless steel or nickel-titanium alloys (e.g. nitinol) may be coated with gold, titanium or platinum. Alloys may also be replaced with pure metals. In still other embodiments, an incompatible metallic or polymeric component is replaced or coated with silica materials or fibers, such as glass or quartz.

Glass or quartz materials appropriate for the practice of the invention include fused silica fibers. Such fused silica fibers are flexible and do not take on a set shape after being bent for a given period of time. According to one embodiment, a lumen made of fused silica fibers can be formed. In certain embodiments, such a lumen of fused silica fibers can be inserted into another outer lumen material, such as a metal lumen or a plastic lumen, which outer lumen would provide additional properties such as stiffness, bonding, color, friction resistance (e.g., PTFE), and so forth. In this way, the pharmaceutically active material that travels through the lumen contacts only the fused silica.

In the case of adhesives, for instance, an incompatible adhesive may be replaced with a more compatible one. For example, as seen in the Examples below, a virally incompatible adhesive, such as FDA2 or FDA23 (epoxy-based adhesives) can be replaced with a more compatible one, such as HB Fuller 3507 (a urethane-based adhesive). As an alternative example, the incompatible adhesive is coated with a more compatible polymer material.

Below are examples of specific embodiments for carrying out the present invention. The examples are offered for illustrative purposes only, and are not intended to limit the scope of the present invention in any way.

EXAMPLES

Example 1

Time Course Evaluation of Virus Compatibility

A CMV-β-gal adenovirus (i.e., an adenoviral vector driven by a CMV (cytomegalovirus) promoter and encoding a β-galactosidase (β-gal) reporter gene) was used as a stock virus in this example.

Stock virus having a viral titer of $3 \times 10^7$ (also referred to herein as $3 \times 10^{\wedge}7$ or 3E+07) infectious units/ml (IU/ml) (also referred to herein as pfu/ml) was incubated in catheters at 37° C. The catheters used were endocardial catheters like those described in international patent application WO/9922655, the disclosure of which is hereby incorporated by reference in its entirety. These catheters have a proximal portion formed from heat-treated stainless steel and a distal portion formed from a nitinol hypotube (referred to in these examples as "catheter" or "injection catheter" or "needle injection catheter"); the hub is comprised of polycarbonate. After the allotted amount of time (0-30 minutes, where 0 minutes refers to the situation in which the viral solution was flushed through the catheter), the viral solution was pushed through the catheter into a polypropylene eppendorf tube. The viral solution was then titered on HeLa cells (human epidermoid carcinoma cells). For this purpose, HeLa cells were first plated out in well plates at 70% confluency the day before the experiment. Prior to contacting the HeLa cells, the viral solution was diluted appropriately in infection media (DMEM (Dulbecco's Modified Eagle's Medium)+2% FBS (Fetal Bovine Serum)) to achieve a result of 1E+02 –1E+03 infected cells per well. The diluted virus was added to the HeLa cells in the wells and incubated at 37° C. for 1 hour. 5 mls of DMEM+ 10% FBS were then added to each well, followed by incubation for 24-30 hours at 37° C. After aspirating of the media, the cells were fixed in 0.5% glutaraldehyde in PBS (phosphate buffered saline) for 10 minutes. The cells were washed twice in PBS and stained using an X-gal staining solution overnight at 37° C. (X-gal is 5-bromo-4-chloro-3-indolyl-β-D-galactoside, which is hydrolyzed by β-galactosidase to form a blue product). Blue cells were counted the next day to determine the titer.

Data are presented in the table to follow for 0 (simple flush through), 5, 10 and 30 minutes in the catheter. The data are presented in the table in terms of cell counts (accounting appropriately for dilution), in terms of absolute titer (IU/ml), and in terms of percentage of the titer of stock virus (3.0E+07 IU/ml).

Figure 2:
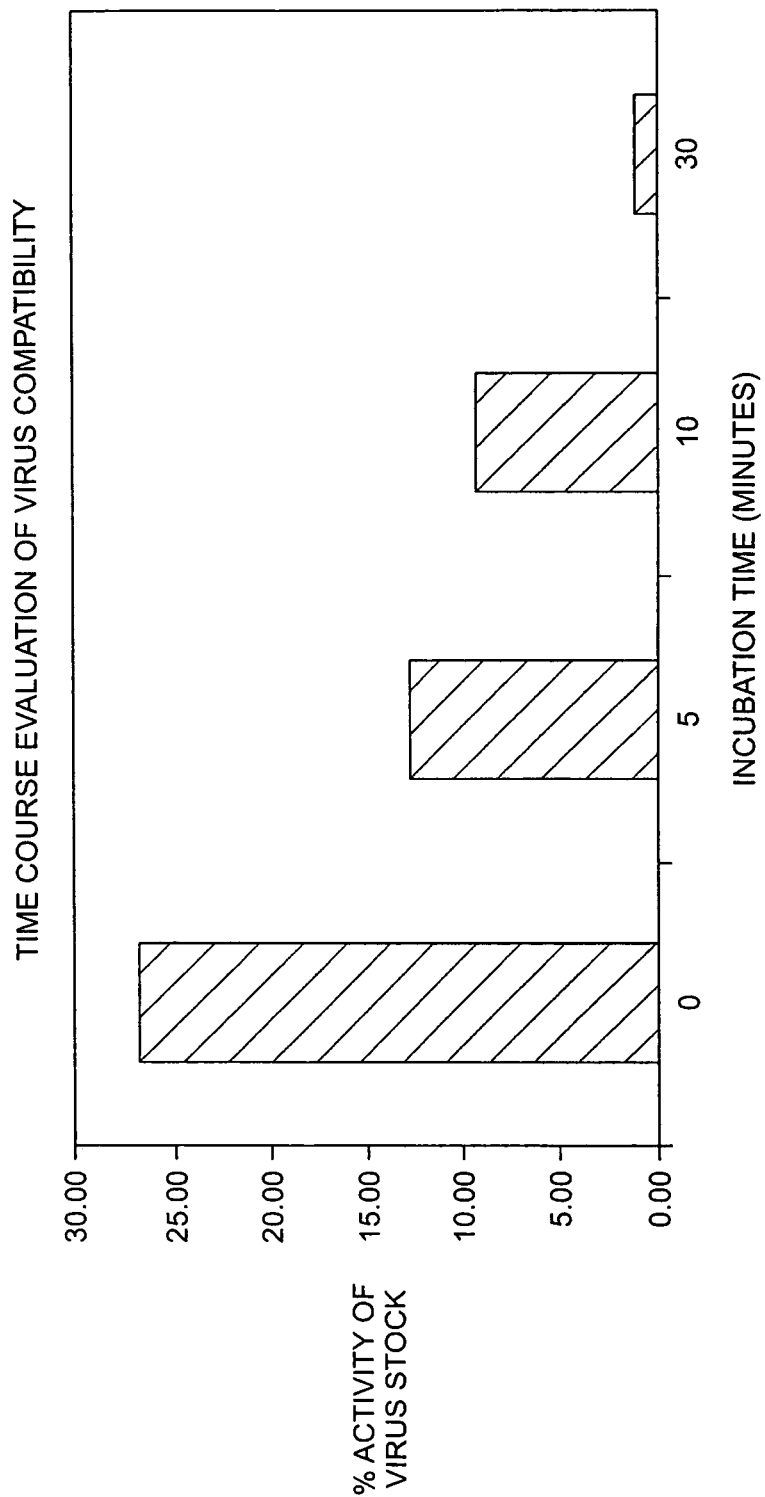
FIG. 2 presents the data of FIG. 1 as a percentage of viral stock titer (linear scale).

FIG. 1 presents these data in terms of absolute virus titer (log scale) and FIG. 2 presents these data relative to the viral stock titer (linear scale). These data suggest that residency in the catheter results in a deterioration of viral efficacy and that this incompatibility effect increases with increasing exposure time.

| Time (min.) | Pos. Cells #1 | Pos. Cells #2 | Pos. Cells #3 | Titer (IU/ml) | Std. Dev. | % of stock |
|---|---|---|---|---|---|---|
| 0 | 7400000 | 10800000 | 5900000 | 8.03E+06 | 2.51E+06 | 26.78 |
| 5 | 3400000 | 4100000 | | 3.75E+06 | 4.95E+05 | 12.50 |
| 10 | 3900000 | 2400000 | 1800000 | 2.70E+06 | 1.08E+06 | 9.00 |
| 30 | 300000 | 300000 | 300000 | 3.00E+05 | 0.00E+00 | 1.00 |

Example 2

Time Course Evaluation of Virus Compatibility

Procedures similar to Example 1 were followed, except that an additional initial viral titer (4E+08 IU/ml) was examined, both in a catheter and as a control. For the control, the virus was exposed to a polypropylene vial for the appropriate period.

The number of positive cells was counted: (1) after 0 (flush through) and 30 minutes in the control vial (4E+08 IU/ml), (2) after 0 (flush through) and 30 minutes in the catheter, using the same stock virus titer as the control (4E+08 IU/ml), and (3) after 0 (flush through) and 30 minutes in the catheter, using a lower stock virus titer (3E+07 IU/ml).

Figure 3:
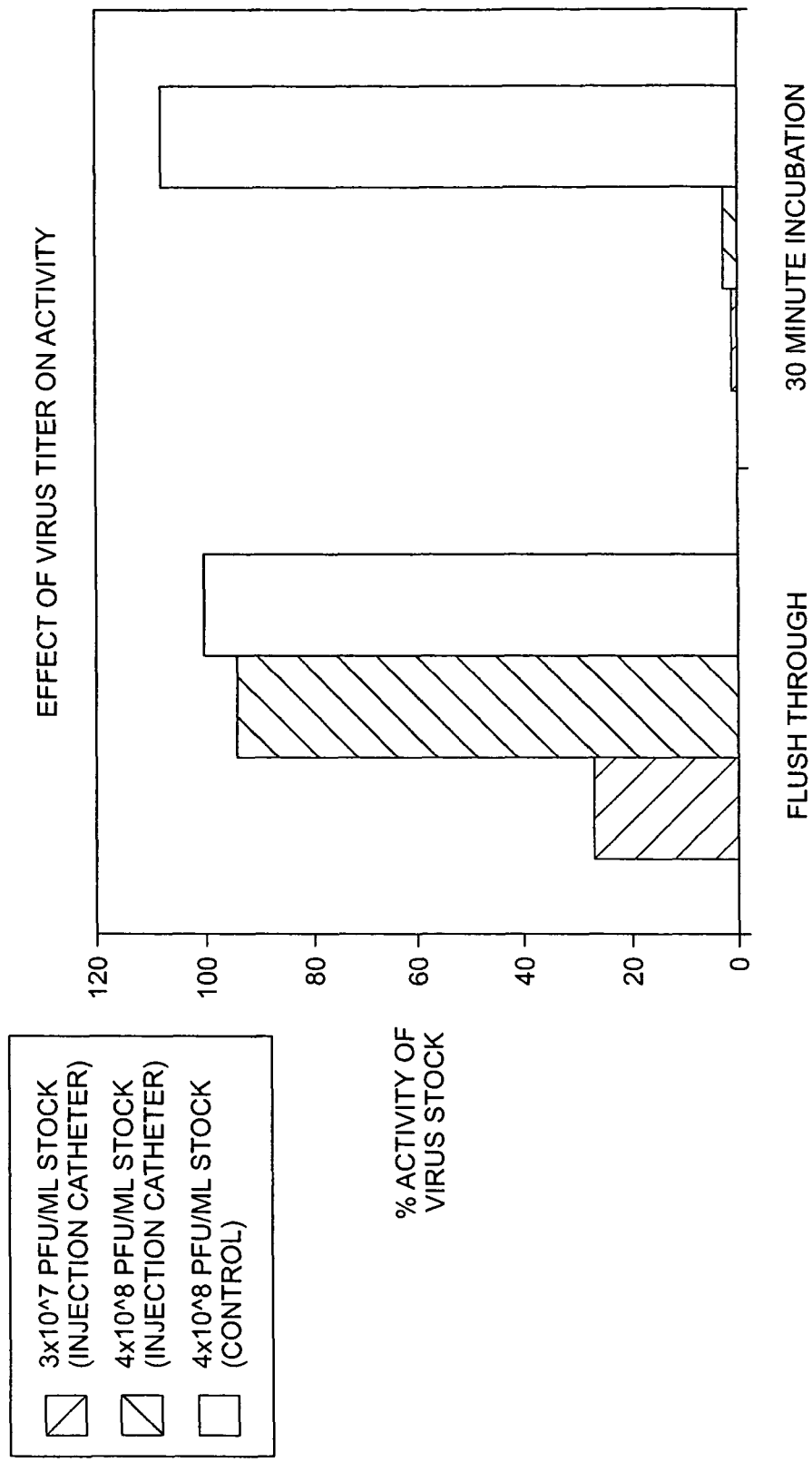
FIG. 3 presents virus titer (as a percentage of virus stock titer): (a) after 0 (flush through) and 30 minutes for a control (4E+08 pfu/ml initial titer), (b) after 0 (flush through) and 30 minutes for an injection catheter constructed of stainless steel and nitinol, using the same stock virus titer as the control (4E+08 pfu/ml initial titer), and (c) after 0 (flush through) and 30 minutes for an injection catheter constructed of stainless steel and nitinol, using a lower stock virus titer (3E+07 pfu/ml initial titer).

Data are presented in FIG. 3, which presents these data as a percentage of viral stock titer. As in Example 1, there is a significant drop in virus activity as a function of incubation time. For a virus stock titer of 3E+07 IU/ml, a flush through resulted in a 75% loss of activity relative to the viral stock while a 30-minute incubation resulted in a 99% loss of activity. At the higher titer of virus, 4E+08 IU/ml, a flush through the catheter resulted in only a 6% loss of activity. However, 97% activity was lost after 30 minutes, consistent with the results at the lower titer. Hence, simply increasing viral titer may not appear to be an effective solution to the loss in viral efficacy observed.

Example 3

Time Course Evaluation

Figure 4:
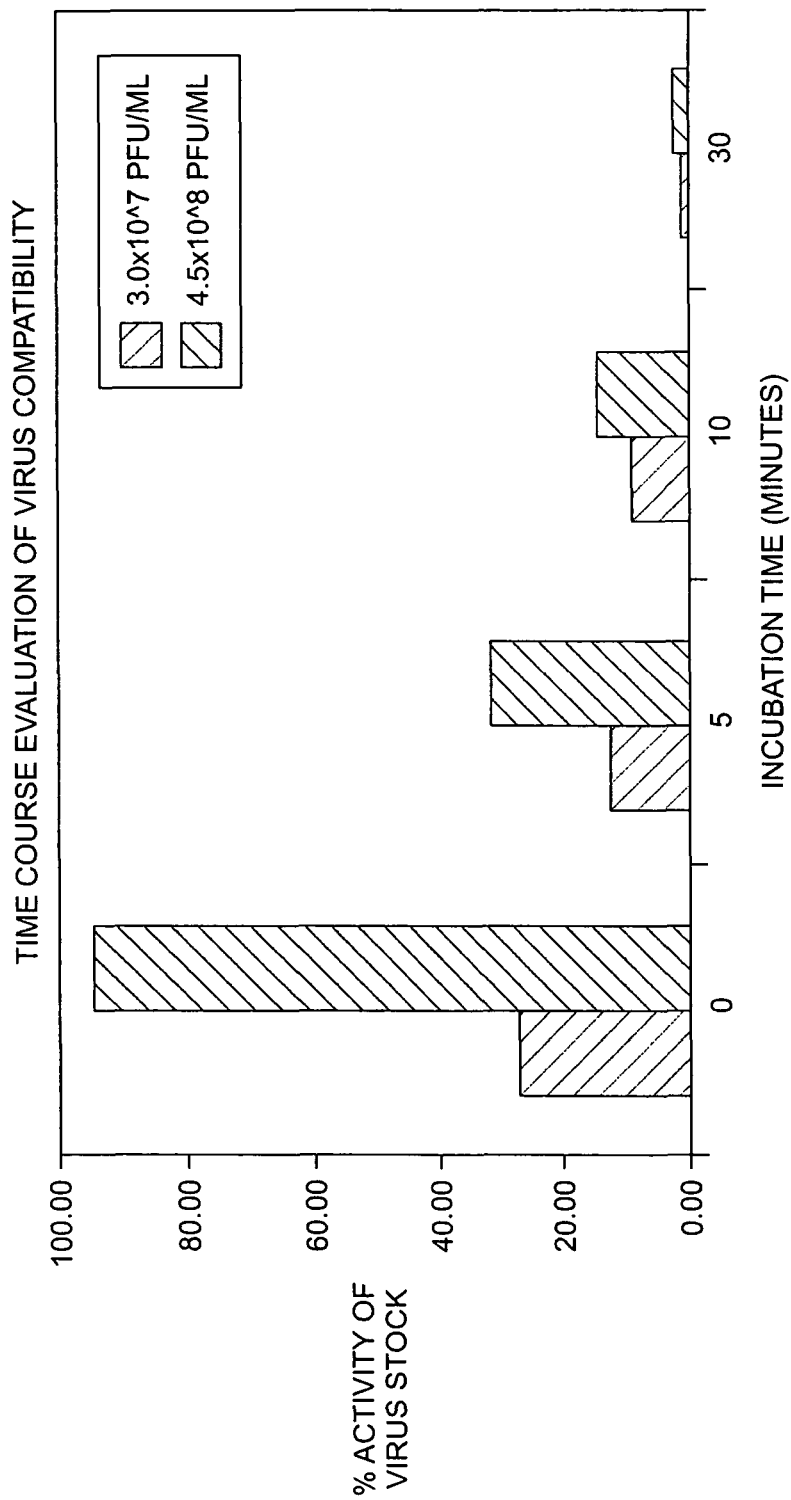
FIG. 4 presents virus titer (as a percentage of virus stock titer) after 0 (flush through), 5, 10 and 30 minutes an injection catheter constructed of stainless steel and nitinol for two viral solutions (3.0E+7 pfu/ml and 4.5E+8 pfu/ml initial titer).

Procedures similar to Examples 1 and 2 were followed for viral solutions having titers of 3.0E+7 IU/ml and 4.5E+8 IU/ml. Positive cells were counted after 0 (flush through), 5, 10 and 30 minutes in the catheter. Data are presented in FIG. 4, which shows a more pronounced drop in activity for the lower concentration over shorter incubation times. This difference, however, becomes less significant at longer incubation times, as also seen in Example 2.

Example 4

Material Compatibility

In this example, the procedures of Example 1 were followed, except viral titers were measured after exposure to various materials for 30 minutes. In some examples, a stock viral titer of 5E+08 was used. In others (namely, the second control, the injection catheter, and the passivated injection catheter), a stock viral titer of 4E+08 was used. For a control, the stock virus was placed in a polypropylene vial for 30 minutes.

The lumen materials for this example have a proximal portion approximately 48" in length and a distal portion measuring approximately 14" in length. The overall length is slightly less than 62", because the distal end is inserted into the proximal end. (Note that Groups #3 and #4 below were single pieces of 5 ft. lengths.)

Figure 7:
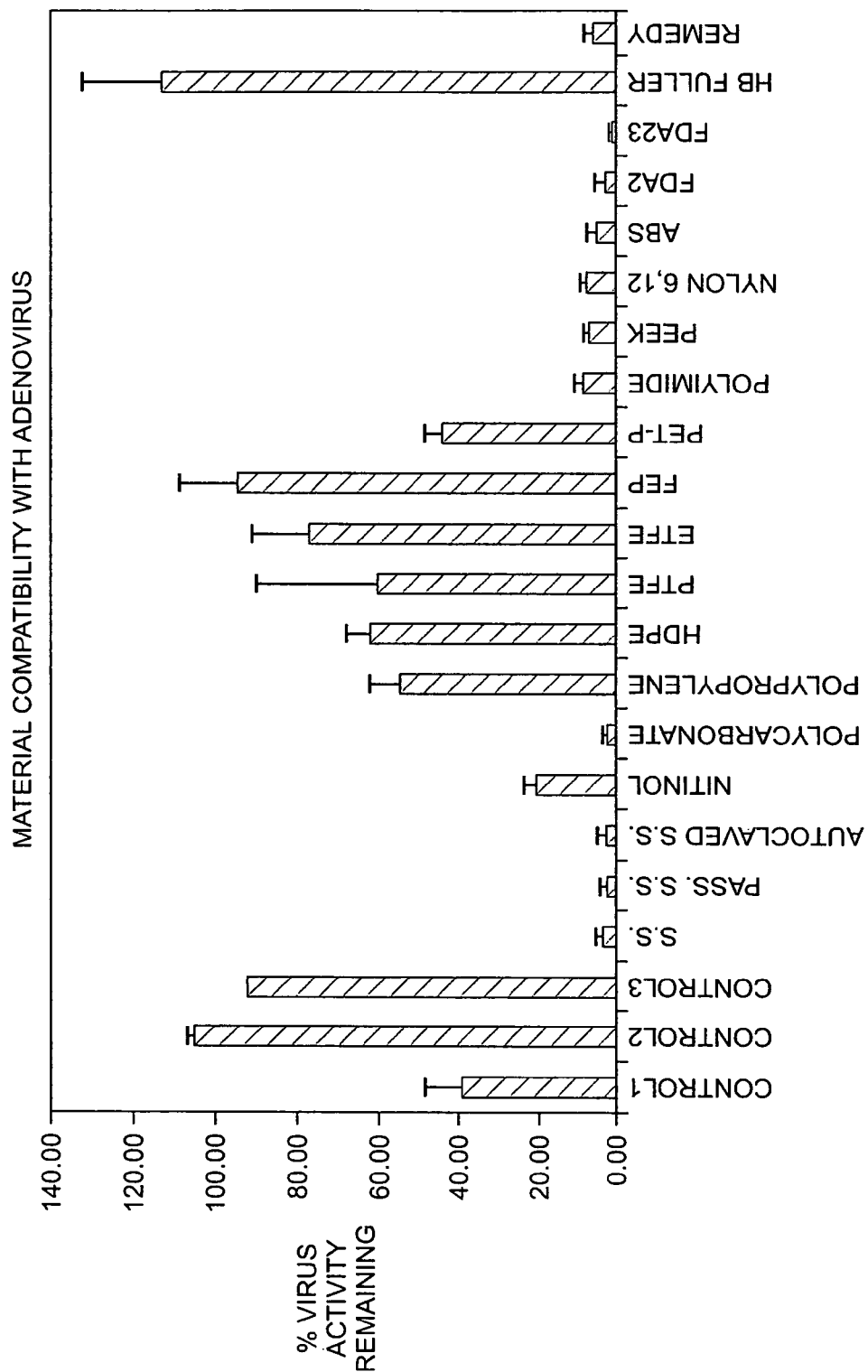
FIG. 7 presents virus titer as a percentage of viral stock titer (linear scale) after 30 minute incubation in connection with the following materials: stainless steel, passivated stainless steel, autoclaved stainless steel, nitinol, polycarbonate, polypropylene, high density polyethylene (HDPE), polytetrafluoroethylene (PTFE), modified ethylene-tetrafluoroethylene copolymer (ETFE), poly(tetrafluoroethylene-co-hexafluoropropene) (FEP), polyethylene terephthalate polyester (PET-P), polyimide, poly ether ether ketone (PEEK), nylon 6/12, acrylonitrile/butadiene/styrene resin (ABS), FDA2, FDA23, HP Fuller, and a REMEDY infusion balloon catheter.

Lumen materials for this example were as follows (dimensions are in inches if not otherwise indicated): (1) injection catheter with a proximal end (0.013"×0.025") formed from heat-treated stainless steel, a distal end (0.009"×0.014") formed from a nitinol hypotube, and containing polycarbonate hub (See Example 1 above); (2) 0.013×0.025 stainless steel hypotube (proximal end) swaged to a 0.007×0.014 stainless steel hypotube (distal end); (3) 0.0093×0.014 nitinol hypotube; (4) 0.010×0.018 stainless steel hypotube; (5) 0.013×0.025 stainless steel hypotube (proximal end) and 0.0093×0.014 nitinol hypotube (distal end); the nitinol was insulated the with a small piece of 0.013×0.024 Cristamid MS1100 (semiaromatic polyamide; Elf Atochem), the larger stainless steel hypotube collar was bonded over the joint; the proximal stainless steel hypotube was not allowed to touch the distal length of nitinol; (6) full length HDPE necked to 0.010×0.015 on the distal end and 0.013×0.025 on the proximal end; (7) injection catheter of group #1, with passivation treatment.

The passivation process was conducted as set forth in ASTM standard A967-96 "Chemical passivation of stainless steel parts". Specifically, the catheter was treated with a 7% weight to volume citric acid solution in water for 7 minutes at 70° C. Immediately after removal from the citric acid solution, the catheter was thoroughly rinsed in water multiple times.

Absolute titers are presented in FIG. 5 (log scale), and titer as a percentage of viral stock are presented in FIG. 6 (linear scale). These data suggest that all of the lumen materials tested had a negative effect on viral efficacy.

In particular, all untreated lumens containing stainless steel (stainless steel per se, stainless steel swaged to nitinol, stainless steel swaged to nitinol with insulated joint and injection catheter) reduced virus activity to only 1-2% of the stock virus titer. Similarly, virus incubated in nitinol retained only 6% of its original activity. Virus incubated within the passivated injection catheter retained 15% of its original activity. 50% of the virus activity was lost post incubation in the polyethylene lumen.

These data suggest that certain metals, such as stainless steel and nitinol, result in substantial loss of viral efficacy as compared to certain polymers, such as polypropylene (control) and polyethylene. The presence of flow in the polymeric and metal lumens versus the lack of flow in the control sample may have negatively impacted virus activity in addition to a detrimental effect as a result of the high surface area to volume ratio with the lumen samples.

Moreover, these data suggest that metal can be passivated by proper chemical treatment. Without wishing to be held to any particular theory, it is believed that the citric acid solution acts to remove free iron and iron oxides and to build up a surface layer comprised primarily of chromium oxides. The resulting surface is non-electrochemically active and is believed to be relatively inert to other chemical and physicochemical interactions.

It is known that joints between dissimilar metals can create a galvanic reaction in the presence of an electrolyte, resulting in the release of free metal ions and that this may be prevented by insulating the joint between the two metals. Hence, these data also suggest that the loss in efficacy seen with lumens having stainless steel/nitinol joints is not due to a galvanic interaction between nitinol and stainless steel, since the data for insulated and uninsulated joints did not statistically differ.

Example 5

Material Compatibility with Adenovirus

In this Example, viral solution, titer=$4.8\times10^8$ IU/ml, was incubated with a ⅜ inch diameter×1 inch long cylindrical material sample for 30 minutes at 37° C. in polypropylene tubes. The control was virus placed in a polypropylene tube without a material sample. The activity of the virus was assessed after the 30-minute incubation period. The results are shown in FIG. 7 and also include a 30-minute incubation within a REMEDY infusion balloon catheter.

Polymeric materials found to be less compatible with virus include LEXAN polycarbonate (available from General Electric), polyimide (VESPEL SP-1; DuPont), poly ether ether ketone (PEEK) (KETRON; DSM Engineering Plastic Products), nylon 6/12 (Poly Penco), and acrylonitrile/butadiene/styrene resin. Polymeric materials that appear to be more virus-compatible include polypropylene, high-density polyethylene (HDPE), virgin polytetrafluoroethylene (PTFE), modified ethylene-tetrafluoroethylene copolymer (ETFE) (TEFZEL; DuPont) and poly(tetrafluoroethylene-co-hexafluoropropene) (FEP) (FEP 100; DuPont). Polyethylene terephthalate polyester (PET-P) (ERTALYTE; DSM Engineering Plastic Products) was also more compatible.

Figure 5:
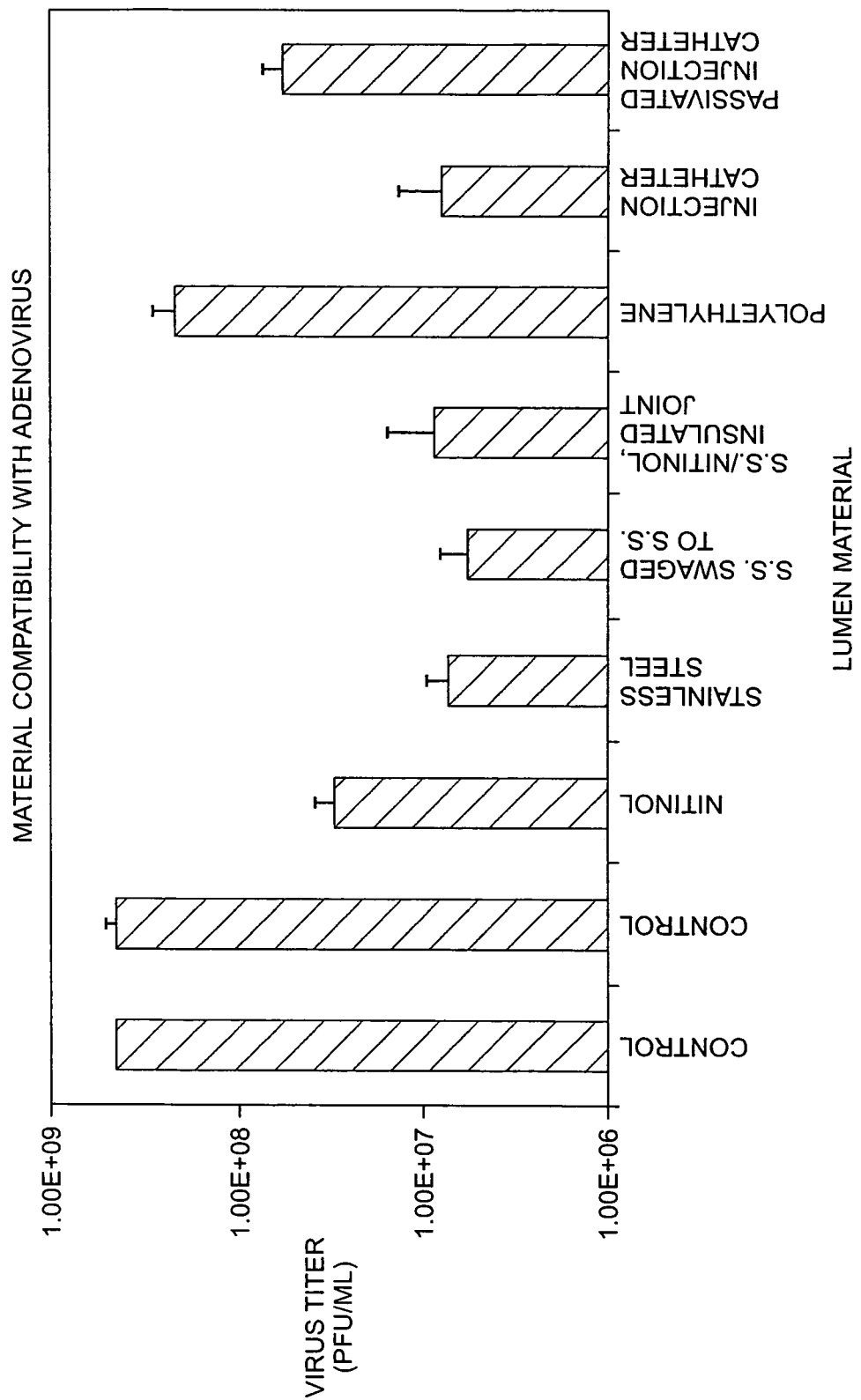
FIG. 5 presents absolute virus titer (log scale) after 30 minute incubation in the following materials: a nitinol lumen, a stainless steel lumen, a lumen of stainless steel swaged to nitinol, a lumen of stainless steel swaged to nitinol with an insulated joint, a polyethylene lumen, an injection catheter constructed of stainless steel and nitinol, and a passivated injection catheter constructed of stainless steel and nitinol.
Figure 6:
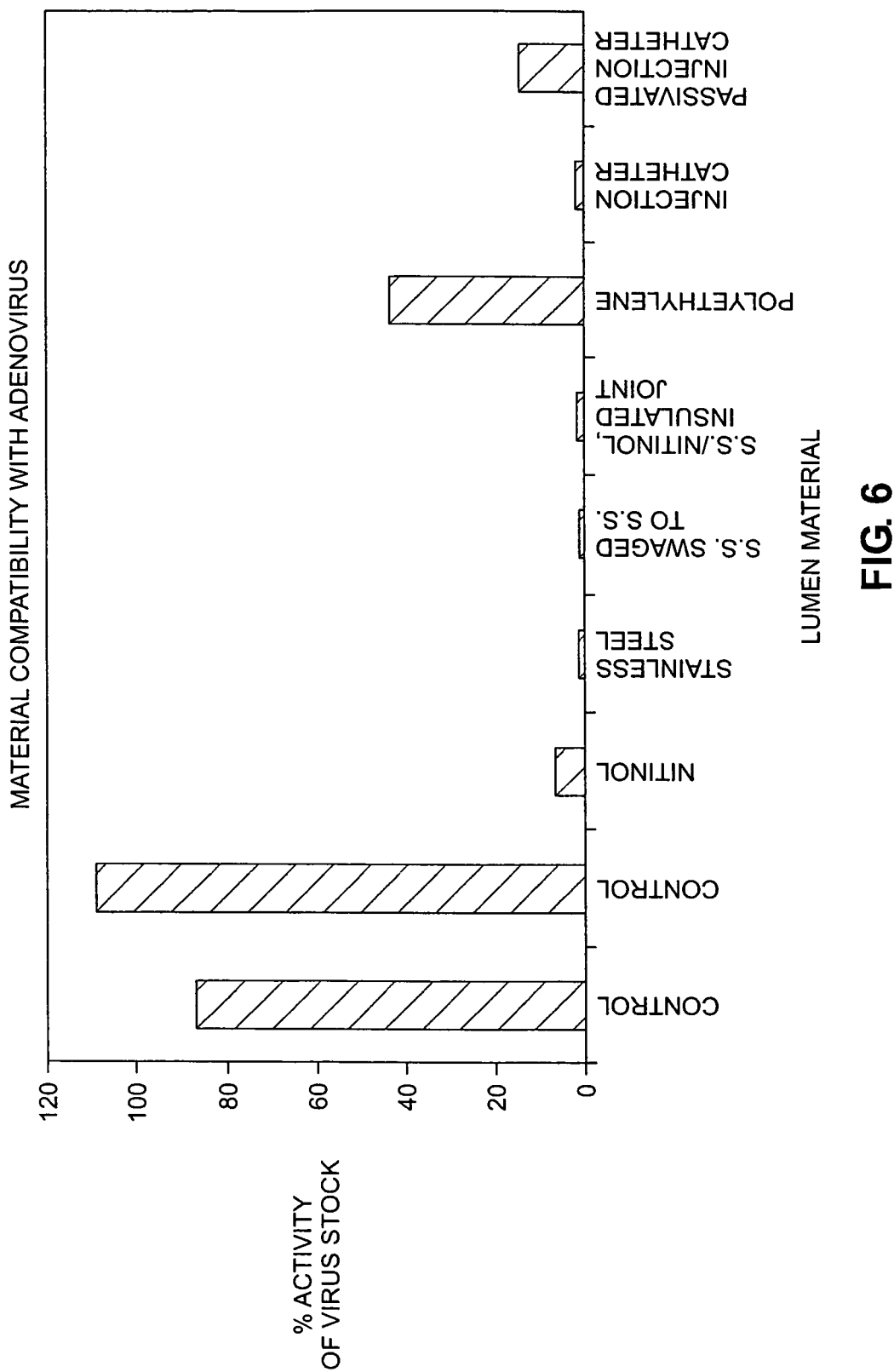
FIG. 6 presents the data of FIG. 5 as a percentage of viral stock titer (linear scale).

Consistent with FIGS. 5 and 6, virus activity dropped significantly in the presence of stainless steel (type 304). The nitinol tested in FIGS. 5 and 6 (available from Raychem Corp. and composed of 55.8% nickel with a balance of titanium) was tested as a catheter including a polycarbonate manifold. Since polycarbonate has been found to be less compatible with virus, the compatibility of Nitinol was uncertain from FIGS. 5 and 6. FIG. 7 indicates that Nitinol is more compatible than stainless steel at 20% activity retained after a 30-minute incubation. However, it is less compatible (statistically significant) than the more compatible polymers apart from PTFE. Among adhesives, HB Fuller 3507 (a urethane-based adhesive available from HB Fuller) was found to be more compatible with virus than FDA2 or FDA23 (epoxy-based adhesives available from Tracon).

Virus incubated within the REMEDY catheter, an infusion balloon catheter available from Boston Scientific Corporation, Natick, Mass., retained only 5% virus activity, consistent with the fact that this catheter contains a polyimide shaft material.

Example 6

Syringe Compatibility with Adenovirus

Figure 8:
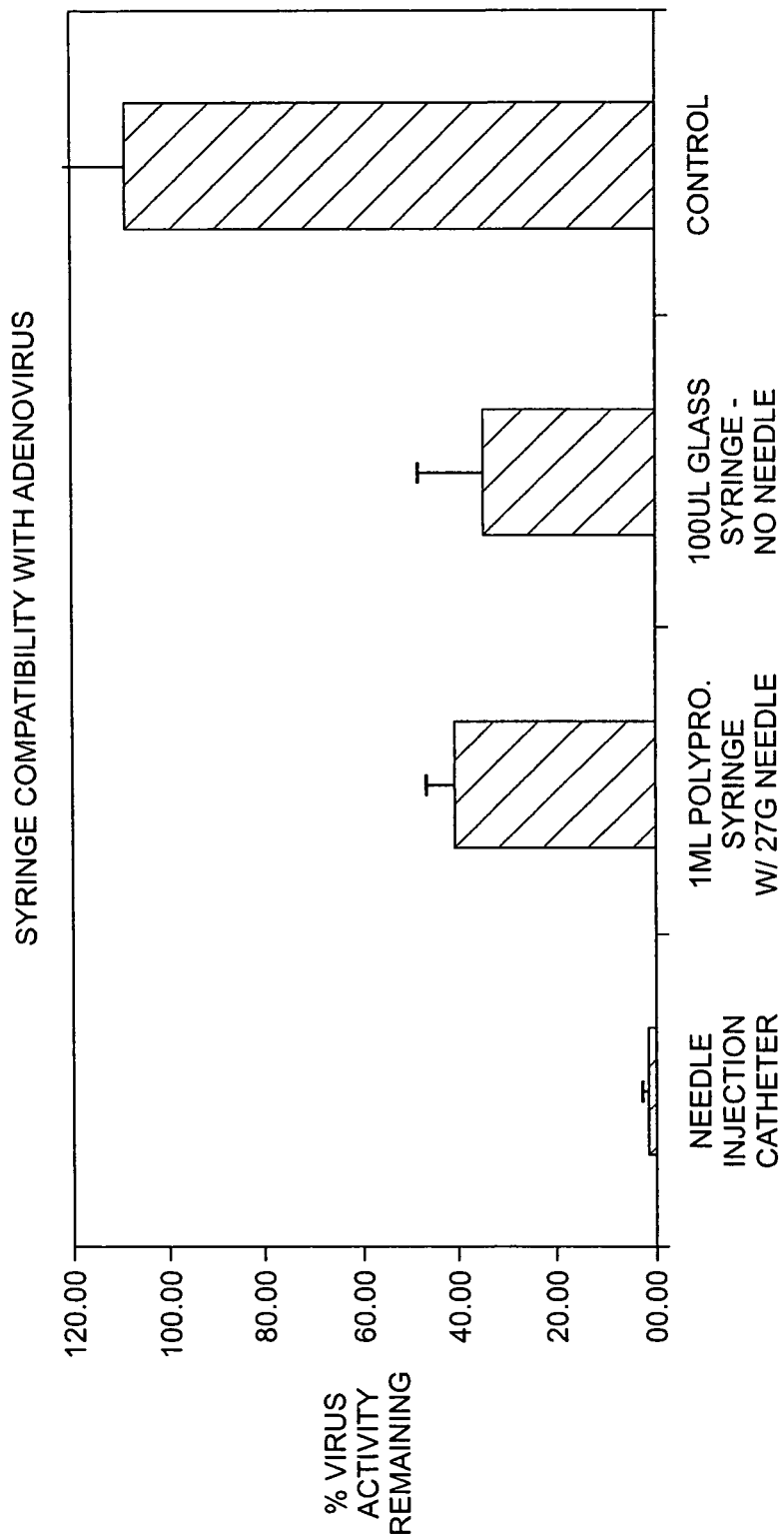
FIG. 8 presents virus titer as a percentage of viral stock titer (linear scale) after 30 minute incubation within a needle injection catheter, a polypropylene syringe (with needle), a glass syringe (without needle) and a control.

Virus solution, initial titer=4.5×10$^8$ IU/ml, was incubated within a needle injection catheter like that of Example 1, within a 1 ml polypropylene syringe with a 27 g needle attached (similar to those commonly used in epicardial injections) and within a 100 µl Oil glass syringe without an attached needle. The control is a polypropylene tube. The results are shown in FIG. 8. This experiment indicates that the glass syringe is comparable to polypropylene, with about 40% virus activity remaining after a 30-minute incubation. Also, virus injection from conventional needle/polypropylene syringe assemblies also result in a reduction of virus activity, potentially due in part to the stainless steel needle.

Example 7

Effect of BSA and PBS Flush on Viral Efficacy

Viral solution (initial titer 5.5×10$^8$) was incubated in a control vial, an untreated needle injection catheter (like that of Example 1), a needle injection catheter treated with BSA (bovine serum albumin) and a needle injection catheter treated with phosphate-buffered saline (PBS). The BSA-treated catheter was provided by flushing a catheter with a 1% aqueous solution of BSA prior to incubation with virus. The PBS treated catheter was similarly flushed with PBS. The stock virus titer for this example was 5.5E+08 IU/ml and the incubation time was 30 minutes.

Figure 9:
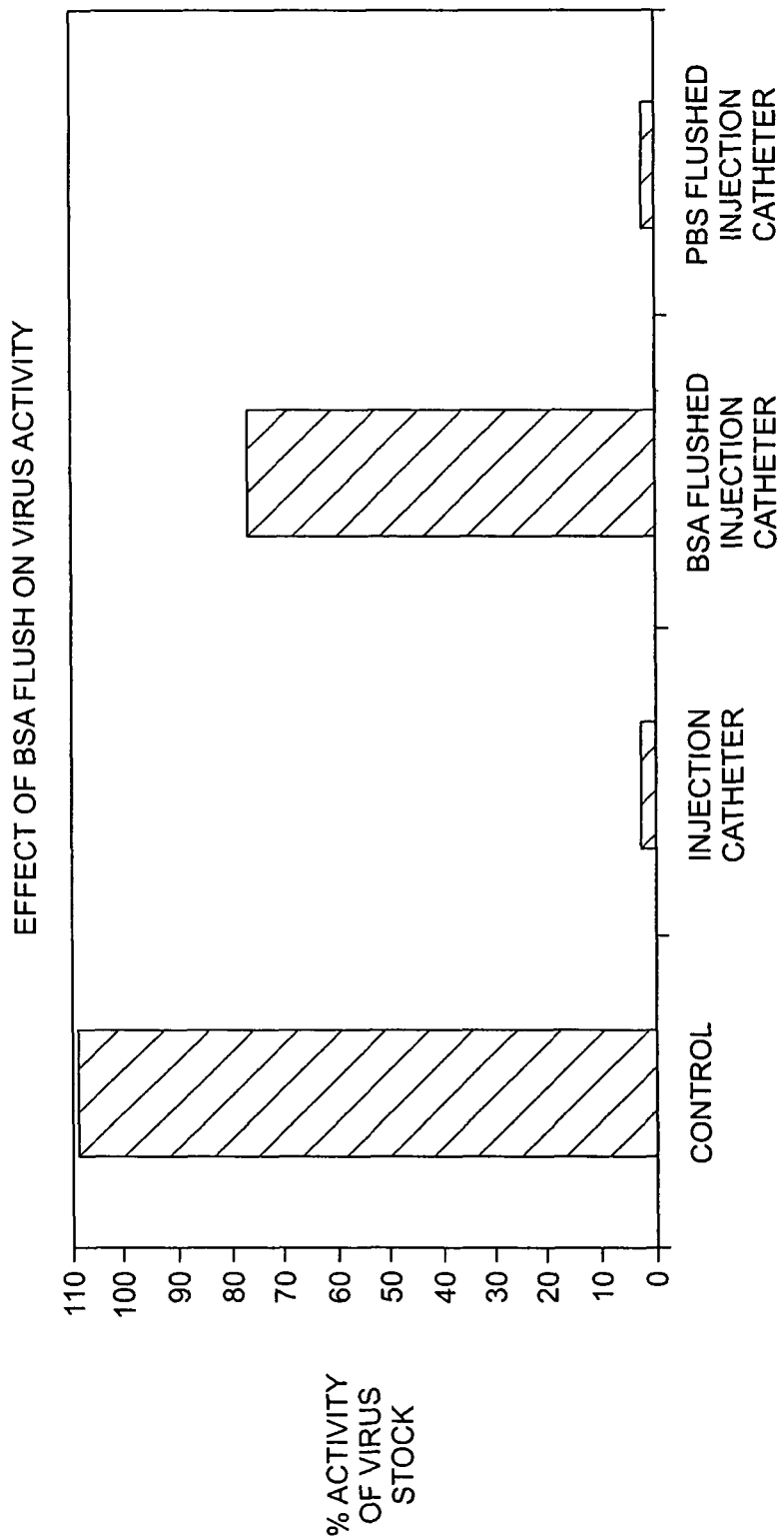
FIG. 9 presents virus titer as a percentage of viral stock titer (linear scale) after 30 minute incubation within a control vial, an untreated needle injection catheter, a needle injection treated flushed with BSA and a needle injection catheter treated with PBS. The BSA- and PBS-treated catheters were provided by flushing with BSA and PBS solutions prior to incubation with virus.

Data are presented in FIG. 9 as a percentage of virus stock titer (linear scale). Virus incubated in the BSA-treated catheter retained 76% of its efficacy, compared to sharp drop in efficacy for the untreated and PBS-treated catheters.

These data suggest that a reduction in viral efficacy in the catheter can be substantially diminished by treatment with BSA. Without wishing to be held to any theory, the albumin may provide a barrier between the metal and virus. Alternatively, dissolved albumin may have a stabilizing effect on the virus in suspension. Therefore, the addition of albumin directly to the virus formulation would be expected to exert a similar effect. The resulting effect would be dependent on the concentration of albumin added to the formulation. These effects are explored in Example 9 below.

Example 8

Effect of HSA and PBS on Virus Activity

Figure 10:
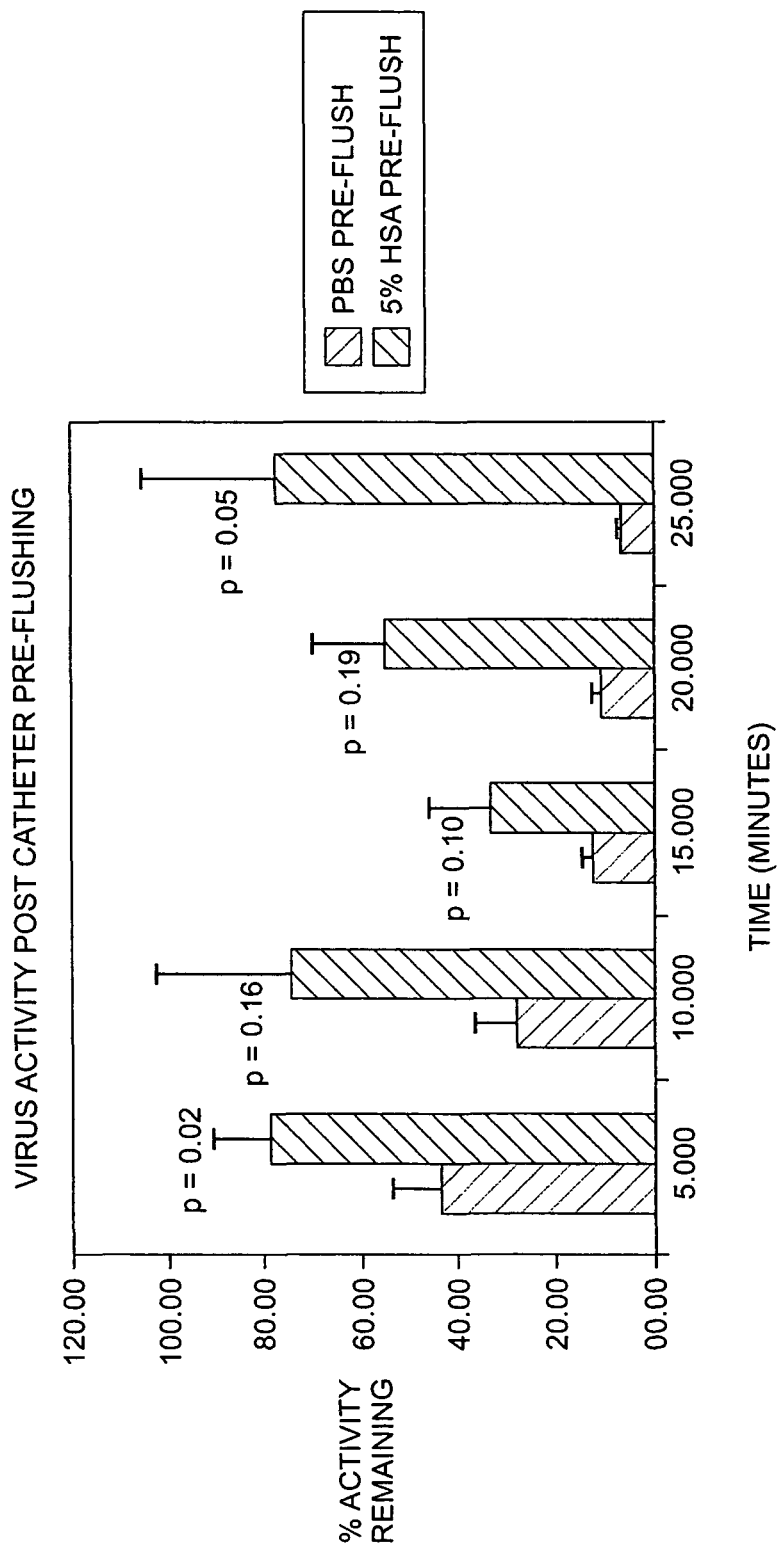
FIG. 10 presents virus titer as a percentage of viral stock titer (linear scale) for needle injection catheters pre-flushed with 5% HSA solution and PBS solution. Viral solution is pushed through the catheters and analyzed at 5, 10, 15, 20 and 25 minutes.

A 5% solution of HSA (human serum albumin) (U.S.P. Albutein 5% Solution, made by Alpha Therapeutic Corporation in Los Angeles, Calif.) was pre-flushed through a needle injection catheter like that of Example 1 prior to virus incubation. Initial viral titer was 5×10$^8$ IU/ml. The catheters were filled, and 50 µl of virus was pushed out of each catheter and assayed after 5 minutes. Additional 50 µl volumes were pushed out every 5 minutes. Since the dead space in the catheter is ~150-160 µl and since the catheter design does not promote back-mixing, one would expect a decrease in virus activity over the first 15 minutes (1$^{st}$ injection resided in the catheter for 5 minutes, 2$^{nd}$ injection resided 10 minutes and 3$^{rd}$ resided 15 minutes) and a leveling off between 15 and 25 minutes (3$^{rd}$ through 5$^{th}$ injections resided in the catheter for a total of approximately 15 minutes). FIG. 10 indicates that a PBS pre-flush does not exert a protective effect on the virus, consistent with the results of the previous example. Additionally, the expected trend as a function of time is indeed observed for the PBS. The HSA pre-flush, however, does preserve virus activity relative to the PBS pre-flush. The protective effect of HSA is sustained through all 5 injections.

Example 9

Effect of HSA Added to Adenovirus Suspension

Figure 11:
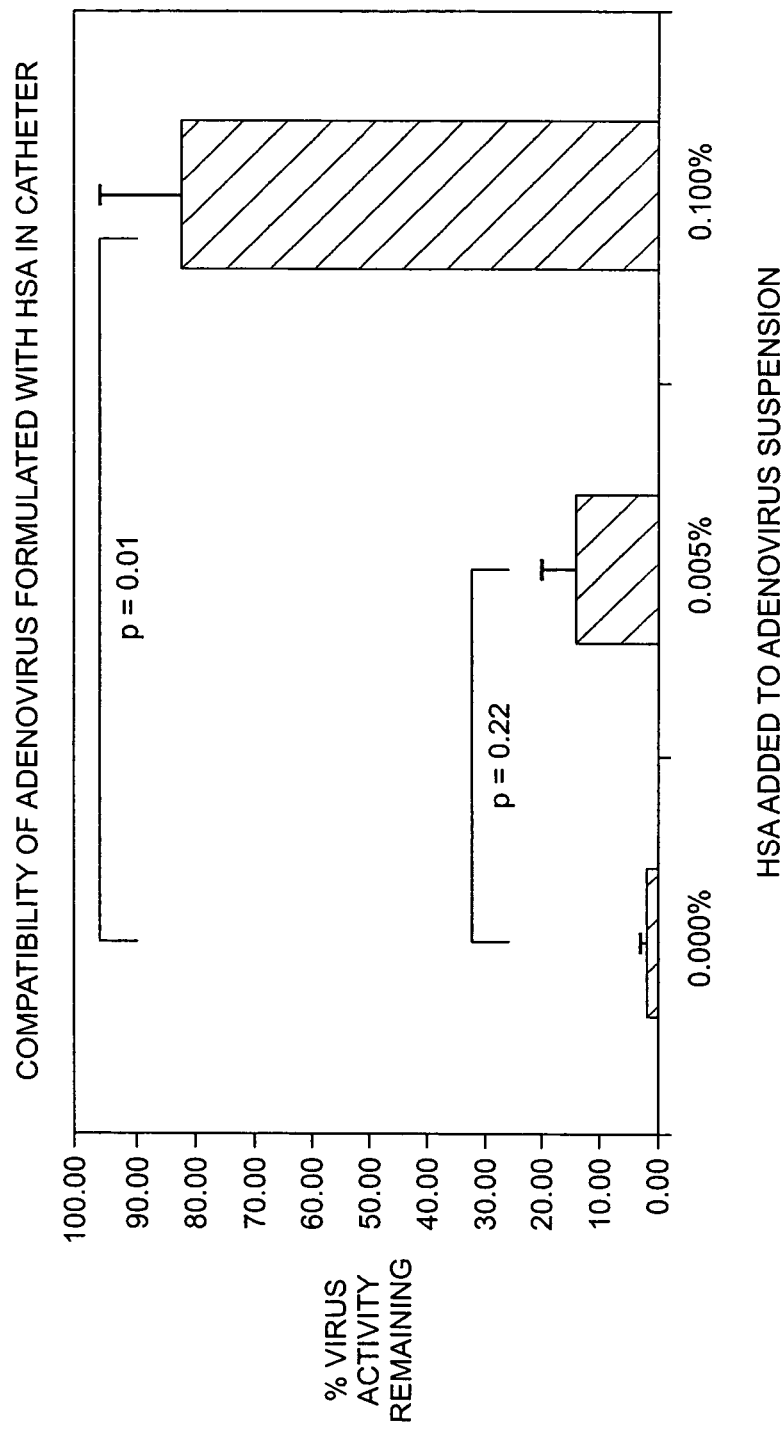
FIG. 11 presents virus titer as a percentage of viral stock titer (linear scale) for adenoviral solutions containing HSA concentrations of 0% (no HSA addition), 0.005% and 0.1%, after incubation within a need injection catheter for 30 minutes.

A 5% solution of HSA (human serum albumin) (U.S.P. Albutein 5% Solution, made by Alpha Therapeutic Corporation in Los Angeles, Calif.) was added to an adenoviral suspension containing 5×10$^8$ IU/ml virus to achieve total HSA concentrations of 0% (no addition), 0.005% and 0.1%, and these suspensions were incubated within a needle injection catheter like that of Example 1 for 30 minutes. The solution was removed and the activity of the adenovirus was assayed. The results are presented in FIG. 11, which demonstrates that the addition of HSA directly to the virus suspension has a concentration-dependent protective effect on adenovirus activity. Adenovirus in a solution of 0.1% HSA has a significantly greater activity (82%) post incubation within the catheter relative to adenovirus without added HSA (1.6%).

Example 10

Viral Adsorption Study

In this example, OD 260 (optical density at a wavelength of 260 nm) data were taken for stock virus, stock virus after 1:10 dilution in PBS, stock virus after flushing it though an injection catheter, stock virus after incubation in an injection catheter for 30 minutes, and stock virus after incubation in polyethylene (high density) for 30 minutes. Stock virus titer in this example was 1E+09 IU/ml.

Figure 12:
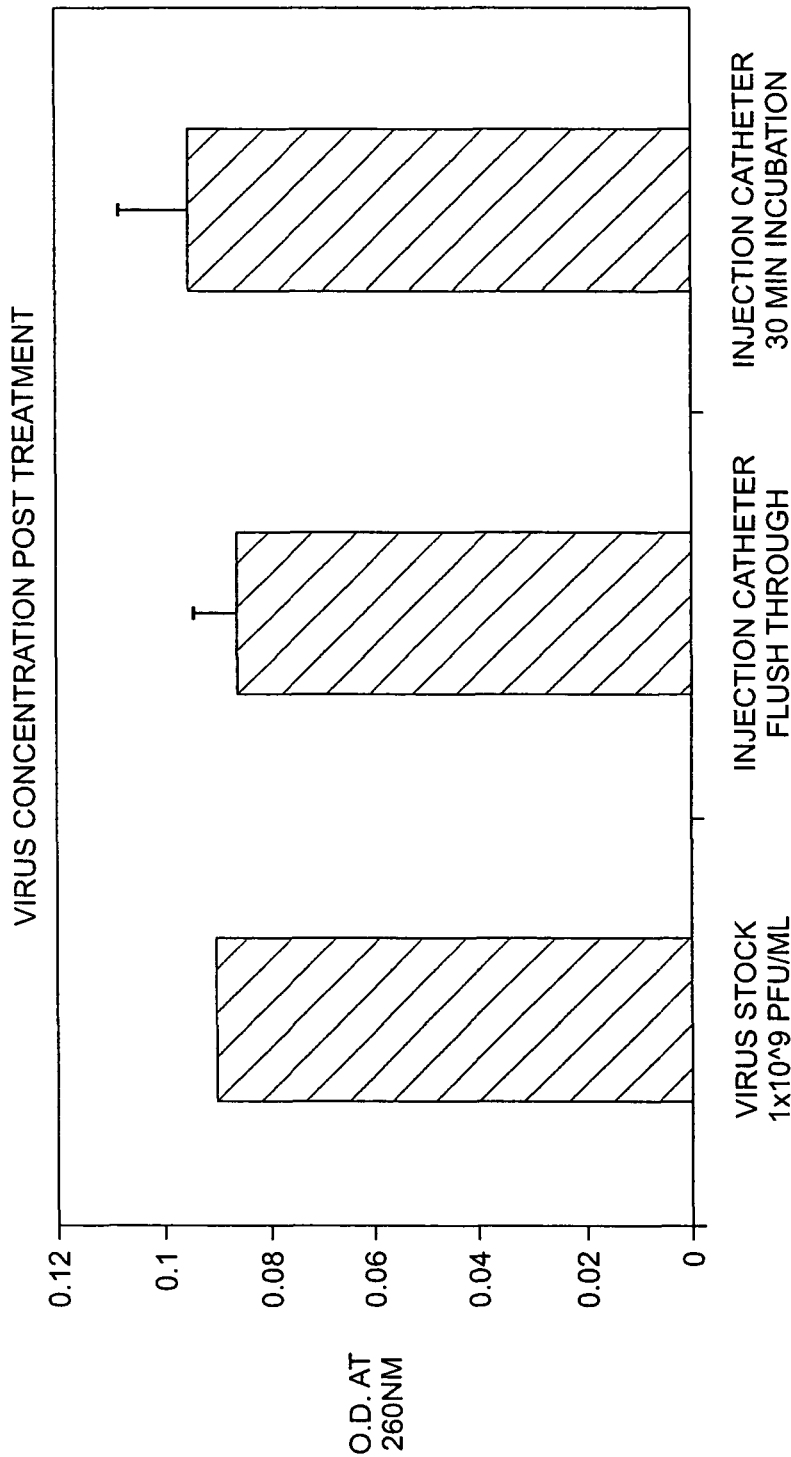
FIG. 12 presents OD 260 data for (a) virus stock, (b) virus stock after flushing through an injection catheter constructed of stainless steel and nitinol, and (c) virus stock after 30 minute incubation in an injection catheter constructed of stainless steel and nitinol.

OD 260 provides data related to viral concentration, which data is independent of its biological activity. OD 260 data for the virus stock (1E+09 IU/ml) without exposure to the catheter (control), after flushing through the catheter, and after an incubation time of 30 minutes in the catheter are presented in FIG. 12. These data suggest that the concentration of viral particles is effectively the same for samples unexposed to the injection catheter, exposed to the injection catheter during the brief flush-through procedure and exposed to the injection catheter for 30 minutes. These data, in combination with data from the examples above, suggest that the catheter does not retain appreciable amounts of virus, in some fashion (e.g., by adsorption), but rather acts predominantly to inactive the virus. (FIG. 13 includes an absorbance value for a 1:10 dilution of the stock virus, indicating the sensitivity of the method.)

Figure 13:
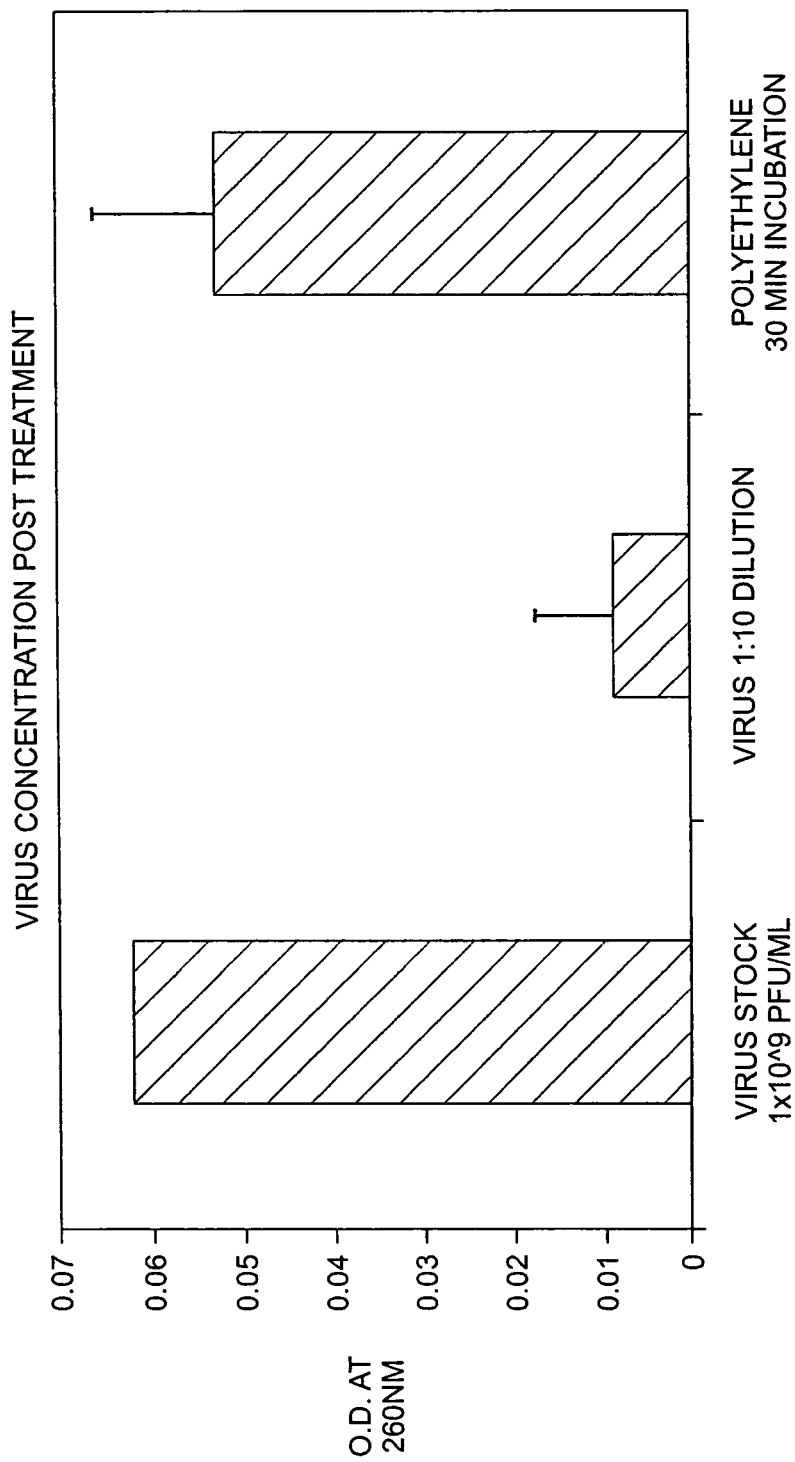
FIG. 13 presents OD 260 data for (a) virus stock (b) virus stock after 1:10 dilution, and (c) virus stock after 30 minutes incubation in a polyethylene lumen.

OD 260 data for virus stock (1E+09 IU/ml), for the virus stock at 1:10 dilution (1E+08 IU/ml), and for the virus stock after incubation in polyethylene for 30 minutes are presented in FIG. 13. As expected, the OD 260 after a 1:10 dilution of the virus stock is on the order of one-tenth that of the undiluted virus stock, according to Beer's Law. Moreover, the differences between the OD 260 of the virus stock and the virus stock after 30 minutes in polyethylene, while different, do not appear to be statistically different. These data, in combination with data from the examples above, suggest that polyethylene may retain virus (e.g., by adsorption), but predominantly acts to inactivate the virus.

Example 11

Viral and Non-viral Vector Activity

Viral and non-viral gene vector solutions were incubated (a) in a polypropylene control vial, (b) in an untreated needle injection catheter like that of Example 1, and (c) in a needle injection catheter like that of Example 1, which has been lined with Pebax® 5533, a polyether block amide. Pebax® polymers are available from Elf-Atochem.

Three gene vector solutions were investigated. The first gene vector solution was an adenoviral vector like that used in Example 1. The second gene vector solution was an adeno-associated viral vector (AAVCMVLacZ) having a titer of $7 \times 10^8$ IU/ml. The third gene vector solution contained 10 µg/ml plasmid vector (a 3958 bp plasmid with the LacZ gene and a CMV promoter/enhancer).

B-galactosidase assays HeLa cells were injected at 70% confluency with either catheter of agent (AdCMV-LacZ, AAVCMV-LacZ, or Plasmid DNA pNGVL-LacZ) in infection media (DMEM+2% FBS) for 1 h at 37 C. Growth medium (DMEM+2% FBS) was added, and the cells were incubated for an additional 24-30 hr at 37° C. Cells were lysed and incubated with O-nitrophenyl beta-D-galactoside to quantify the beta-galactosidase.

Sample titers were interpolated from a calibration curve and agent activity was expressed relative to the polypropylene control groups. Data are presented in FIG. 14a as a percentage of vector stock titer (linear scale). The untreated catheter is designated G1-Stiletto in FIG. 14a, while the Pebax®-treated catheter is designated G2-Stiletto. Both viral gene vectors incubated in the Pebax®-lined catheter resulted in significantly greater activity relative to the catheter without the Pebax® lining. While comparison of plasmid DNA did not reveal significant differences in transfection efficiency between the catheters, there is evidence of structural damage to the plasmid DNA upon incubation in the unlined catheter, which is observed as an increase in the amount of nicked DNA, which runs at a higher apparent molecular weight. Specifically, FIG. 14b is an assessment of plasmid DNA structural integrity using gel electrophoresis. Lanes C1-C2: polypropylene control samples; lanes 1-5: unlined catheter; lanes 6-10 Pebax lined catheter. Each lane represents effluent from a single catheter (n=5 per catheter group). The unlined catheter samples show ingrowth of an apparently higher molecular weight band, which is indicative of structural damage to the DNA (i.e. nicking of the circular DNA).

These data indicate that a reduction in vector efficacy in the catheter is observed for a broad range of vector types and that this reduction can be substantially diminished by providing an appropriate lining within the catheter.

Example 12

Cell Viability

Cardiomyogenic cells (CMG) were plated at approximately 200,000 per 10 cm plate, cultured in Iscove's modified Dulbecco's medium (DMEM) (Gibco BRL Cat. #12440-053) supplemented with 20% heat-inactivated fetal calf serum (Summit Biotechnology, Fort Collins Colo., Cat. #FP-100-05, lot FA1015), penicillin-streptomycin (100 U/mL 100 mg/mL) (Gibco BRL Cat. #14040-133), glutamine (2 mM) (Gibco BRL Cat. #25030-081), and maintained at 5% $CO_2$, 33° C. Prior to harvesting cells for experimentation, cells were briefly treated with trypsin, and the trypsin was inactivated in excess growth medium. Cells were collected by centrifugation, counted, and resuspended in Dulbecco's phosphate-buffered saline (DPBS) with $Mg^{2+}/Ca^{2+}$ (Gibco BRL, Cat. #14040-133) at the concentration indicated in the text. This cell-containing PBS solution was kept on ice. The cell suspension was loaded into the catheters, incubated for 30 minutes at 37° C., recovered from the catheters using an air-filled syringe, and counted. Cell viability was determined by Trypan Blue dye exclusion. The number of viable cells recovered from the catheters was normalized to that obtained from controls consisting of cells subjected to a 30 minute incubation at 37° C. following loading into Eppendorf microcentrifuge tubes. All results are expressed as a mean+/− SEM, and comparisons were analyzed using ANOVA and Student's T-test. P<0.05 was considered statistically significant. All statistical data were analyzed using Microsoft Excel (Redmond, Wash.).

Data are presented in FIG. 15 as a percentage of viable cell recovery (linear scale). In all cases, cells incubated in the Pebax®-lined catheter (designated G2-Stiletto in FIG. 15) retained greater activity relative to the catheter without the Pebax® lining (designated G1-Stiletto in FIG. 15). This effect is more pronounced at lower cell concentrations ($5 \times 10^5$ cells/ml) than it is at higher cell concentrations ($5 \times 10^6$ cells/ml).

These data indicate that, in addition to adversely affecting gene vector efficacy as discussed above, the catheter also adversely affects the efficacy of whole cells. As with the previous data, these data further indicate that the adverse effects of the catheter can be substantially diminished by providing an appropriate lining within the same.

Example 13

Buffer Effects

Four viral solutions, each with an initial titer of $1 \times 10^9$ IU/ml, were incubated for 30 minutes within (a) a needle injection catheter like that of Example 1 and (b) a needle injection catheter like that of Example 1 that has been lined with Pebax® 5533. The following buffer solutions were used for the viral solutions: (1) a solution of 0.1% glycerol in PBS, (2) a solution of 10% glycerol in 10 mM tris(hydroxymethyl) aminomethane buffer, (3) a solution of 4% sucrose in PBS and (4) a solution of 4% sucrose in 10 mM tris(hydroxymethyl) aminomethane buffer. The control was a polypropylene tube.

Data are presented in FIG. 16 as a percentage of virus stock titer (linear scale). This experiment indicates that a reduction in gene vector efficacy in the catheter extends over a broad range of buffer systems and, as above, that this reduction can be substantially diminished by providing the catheter with an appropriate lining.

Example 14

Polyether Block Imide and Silicone as Barrier Layers

A viral solution with an initial titer of $1\times10^9$ IU/ml was exposed to various substrates for 30 minutes. The substrates were as follows: (1) a stainless steel hypotube (0.013 inch ID×0.025 inch OD×30 cm length) coated with a mixture of Dow Corning MDX4, an amino-functional silicone, and 360 Medical Fluid, a linear silicone that serves as a plasticizer; (2) a stainless steel hypotube (0.013 inch ID×0.025 inch OD×30 cm length) coated with one application of a 5% MDX4 solution only; (3) a stainless steel hypotube (0.013 inch ID×0.025 inch OD×30 cm length) coated with methyltriacetoxysilane, a low molecular weight silane; (4) a stainless steel hypotube (0.013 inch ID×0.025 inch OD×30 cm length) coated with Pebax® 5533; (5) a 0.013 inch×0.025 inch×ca. 30 cm stainless steel hypotube; (6) a 0.0093 inch×0.014 inch×30 cm nitinol hypotube and (7) a nitinol hypotube (0.0093 inch× 0.014 inch×ca. 30 cm) coated with Pebax® 5533. The control is a polypropylene tube. After incubation, vector activity was assessed using the techniques of Example 11.

Data are presented in FIG. 17 as a percentage of virus stock titer (linear scale). This experiment, along with FIG. 6, which contains data for the uncoated stainless steel and nitinol lumens, demonstrates that there is a reduction in vector efficacy for both stainless steel and nitinol, and that this reduction can be substantially diminished by providing an appropriate coating.

Example 15

Effect of Catheter Shaft Construction on Viral Efficacy

A viral solution with an initial titer of $1\times10^9$ IU/ml was exposed to various catheter constructions for 30 minutes. The predominant material in these catheter constructions is the shaft material. Shaft materials are as follows: (1) stainless steel, (2) polyether block amide (Pebax® 5533 available from Elf Atochem), (3) polyethylene (Chevron 9640 from Chevron Phillips), (4) polyimide, (5) polyether block amide (Pebax® 7033 available from Elf Atochem), and (6) polyethylene. The control is a polypropylene tube. After incubation, vector activity was assessed using the techniques of Example 1.

Data are presented in FIG. 18 as a percentage of virus stock titer (linear scale). Dramatic reductions in vector efficacy are seen for catheters with stainless steel and polyimide shafts. On the other hand, with catheters having polyether block amide shafts and polyethylene shafts, the reductions observed are less dramatic, if present at all. These data are consistent with the data found, for example, in FIG. 7.

Example 16

Material Compatibility with Adenovirus

In this Example, an adenoviral viral solution with an initial titer of $1\times10^9$ IU/ml was incubated with lumen sample material for 30 minutes at 37° C. Lumen materials are as follows: (1) a stainless steel hypotube (0.013 ID×0.025 OD×30 cm length), (2) Pebax® 2533, a polyether block amide, tubes (0.0192" ID×0.0352" OD, ca 20" length available from Elf Atochem, (3) tubes (0.0192" ID×0.0352" OD, ca 20" length) of Pebax® 5533, a polyether block amide available from Elf Atochem, (4) tubes (0.0192" ID×0.0352" OD, 20" length) of Pebax® 7033, a polyether block amide available from Elf Atochem, (5) tubes (0.024" ID×0.027" OD, 21.5" length) of Arnitel EM550, a polyether ester available from DSM, (6) tubes (0.022"×0.046", 12.5" length) of Arnitel EM740, a polyether ester available from DSM, (7) tubes (0.027 inch ID×0.037 inch OD, 12.5" length) of Hytrel 7246, a polyester available from Dupont, (8) tubes (0.025 inch ID×0.034 inch OD, 12.5" length) of Cristamid MS1100, an amorphous nylon polymer available from Elf Atochem, and (9) tubes (0.025 inch ID×0.034 inch OD, 12.5" length) of Rilsan Aesno Nylon 12 available from Elf Atochem. After incubation, vector activity was assessed using the techniques of Example 11.

Data are presented in FIG. 19 as a percentage of virus stock titer (linear scale). In general, polymeric materials show a significant improvement in virus compatibility as compared to stainless steel. However, amongst the polymeric materials the polyether amides (Pebax® family) and polyether/esters preserve virus activity significantly better than the nylon (Cristamid).

Example 17

Effect of Fluoropolymer on Adenovirus Compatibility

In this Example, an adenoviral solution with an initial titer of $1.0\times10^9$ IU/ml, was incubated for 30 minutes at 37° C. in association with the following: (1) needle injection catheter, like that of Example 1, (2) a PTFE plug (⅜ inch diameter×1 inch long cylinder), (3) an FEP plug (⅜ inch diameter×1 inch long cylinder) (4) a 0.013 inch ID×0.025 inch OD×30 cm length tube coated with Xylan-8110, a PTFE polymer available from Whitford Co in a coating formulation available from Thermech, (5) a 0.013 inch ID×0.025 inch OD×30 cm length tube coated with Xylan-1220, a FEP polymer available from Whitford Co., which is formulated in a coating available from Thermech, (6) a 0.013 inch ID×0.025 inch OD×30 cm length tube constructed from FEP available from Endura, (7) a stainless steel tube lined with PTFE liner (ca 0.01" ID), (8) a lumen of PTFE having an internal diameter of 0.012 inch, (9) a lumen of PTFE having an internal diameter of 0.015 inch. The control is a polypropylene tube. After incubation, vector activity was assessed using the techniques of Example 1.

Data are presented in FIG. 20 as a percentage of virus stock titer (linear scale).

The virus compatibility experiments revealed no significant difference between these teflon-coated surfaces and the bare needle injection catheter. Elemental analysis (ICP and X-ray diffraction) of the lumens detected a spectrum of metal species (Cr, Fe, Mn, Ni, and Ti) on all coated surfaces.

Although the ICP results varied within a treatment group (also observed for the uncoated lumen group), these results indicate that the inner lumens are heterogeneous surfaces. Most importantly, and corroborated by the SEM-X-ray analysis, the teflon-covered were not adequately coated. Recognizing the inherent difficulty in coating the narrow, 0.009" inner lumen, a teflon-lined polyimide lumen was extruded and tested. Nonetheless, loss of virus activity was still observed. It is known, however, that the processing of fluorinated polymers into catheter shafts requires the addition of additives. These materials, which include xylene, glycerine and octylphenoxypolyethoxyethanol, may have a significant effect on virus compatibility, highlighting the importance of testing the complete article components for biological activity.

The present invention provides methods and devices for the delivery of pharmaceutically active materials that overcome incompatibility problems of the prior art. Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

We claim:

1. A modified medical device for delivery of a pharmaceutically active material comprising:
   (a) an incompatible polymeric delivery lumen which acts to substantially reduce pharmaceutical effectiveness of said pharmaceutically active material upon contact with said pharmaceutically active material; wherein said incompatible polymeric delivery lumen is modified by providing it with a layer of polymeric material such that said substantial reduction in the pharmaceutical effectiveness of the pharmaceutically active material is diminished upon contact with said drug delivery lumen; and
   (b) said pharmaceutically active material, wherein said polymeric lumen comprises a polymer selected from a polycarbonate, a polyimide, an acrylonitrile/butadiene/styrene copolymer, a poly ether ether ketone, an epoxy and a nylon.

2. The modified medical device of claim 1, wherein said medical device is a vascular catheter.

3. The modified medical device of claim 2, wherein said vascular catheter is an injection catheter.

4. The modified medical device of claim 2, wherein said vascular catheter is a percutaneous myocardial revascularization catheter.

5. The modified medical device of claim 1, wherein said layer of polymeric material comprises a synthetic polymer.

6. The modified medical device of claim 5, wherein said synthetic polymer is selected from a polyalkylene and a fluorocarbon polymer.

7. The modified medical device of claim 5, wherein said synthetic polymer is selected from low density polyethylene, high density polyethylene, polypropylene, polytetrafluoroethylene, poly(tetrafluoroethylene-co-hexafluoropropene), modified ethylene-tetrafluoroethylene copolymer, ethylene chlorotrifluoroethylene copolymer and polyvinylidene fluoride.

8. The modified medical device of claim 5, wherein said synthetic polymer is selected from polyether block amide, silicone polymer and polypropylene.

9. The modified medical device of claim 5, wherein said layer of polymeric material is provided by coating the incompatible polymeric delivery lumen with uncured polymer, and curing said uncured polymer.

10. The modified medical device of claim 9, wherein said polymer is a silicone resin.

11. The modified medical device of claim 5, wherein said layer of polymeric material is provided in the form of a preformed tube.

12. The modified medical device of claim 1, wherein said pharmaceutically active material comprises a virus or virus-like particles.

13. The modified medical device of claim 1, wherein the pharmaceutically active material comprises a polynucleotide.

14. The modified medical device of claim 13, wherein the pharmaceutically active material comprises naked DNA.

15. The modified medical device of claim 13, wherein the pharmaceutically active material comprises a viral vector.

16. The modified medical device of claim 15, wherein the viral vector is an adenoviral vector.

17. The modified medical device of claim 13, wherein the pharmaceutically active material comprises a non-viral vector.

18. The modified medical device of claim 1, wherein said pharmaceutically active material comprises a protein.

19. The modified medical device of claim 1, wherein said pharmaceutically active material comprises cells.

20. The modified medical device of claim 19, wherein said cells comprise autologous human cells.

21. The modified medical device of claim 19, wherein said cells comprise allogeneic human cells.

22. The modified medical device of claim 19, wherein said cells comprise genetically engineered cells.

23. A modified medical device for delivery of a pharmaceutically active material comprising:
   (a) an incompatible polymeric delivery lumen which acts to substantially reduce pharmaceutical effectiveness of said pharmaceutically active material upon contact with said pharmaceutically active material; wherein said incompatible polymeric delivery lumen is modified by providing it with a layer of polymeric material such that said substantial reduction in the pharmaceutical effectiveness of the pharmaceutically active material is diminished upon contact with said drug delivery lumen; and
   (b) said pharmaceutically active material, wherein said medical device is a vascular catheter, wherein said polymeric lumen comprises a polymer selected from a polycarbonate, a polyimide, an acrylonitrile/butadiene/styrene copolymer, a poly ether ether ketone, an epoxy and a nylon.

24. A modified medical device for delivery of a pharmaceutically active material comprising:
   (a) an incompatible polymeric delivery lumen which acts to substantially reduce pharmaceutical effectiveness of said pharmaceutically active material upon contact with said pharmaceutically active material; wherein said incompatible polymeric delivery lumen is modified by providing it with a layer of polymeric material such that said substantial reduction in the pharmaceutical effectiveness of the pharmaceutically active material is diminished upon contact with said drug delivery lumen; and
   (b) said pharmaceutically active material, wherein the pharmaceutically active material is selected from a protein, and cells, wherein said polymeric lumen comprises a polymer selected from a polycarbonate, a polyimide, an acrylonitrile/butadiene/styrene copolymer, a poly ether ether ketone, an epoxy and a nylon.

25. The modified medical device of claim 24, wherein said medical device is a vascular catheter.

26. The modified medical device of claim 24 wherein said vascular catheter is an injection catheter.

27. The modified medical device of claim 24, wherein said layer of polymeric material comprises a synthetic polymer.

28. The modified medical device of claim 27, wherein said synthetic polymer is selected from a polyalkylene and a fluorocarbon polymer.

29. The modified medical device of claim 27, wherein said synthetic polymer is selected from polyether block amide, silicone polymer and polypropylene.

* * * * *